(12) United States Patent
Bartov et al.

(10) Patent No.: US 11,462,300 B2
(45) Date of Patent: Oct. 4, 2022

(54) METHODS AND SYSTEMS FOR SEQUENCE CALLING

(71) Applicant: Ultima Genomics, Inc., Newark, CA (US)

(72) Inventors: Avishai Bartov, Hod-Hashron (IL); Yoav Etzioni, Tel Aviv (IL); Mark Geshel, Kfar Saba (IL); Mark Pratt, Bozeman, MT (US); Gilad Almogy, Palo Alto, CA (US)

(73) Assignee: Ultima Genomics, Inc., Newark, CA (US)

( * ) Notice: Subject to any disclaimer, the term of this patent is extended or adjusted under 35 U.S.C. 154(b) by 0 days.

(21) Appl. No.: 17/397,802

(22) Filed: Aug. 9, 2021

(65) Prior Publication Data

US 2021/0366576 A1 Nov. 25, 2021

Related U.S. Application Data

(63) Continuation of application No. PCT/US2020/021909, filed on Mar. 10, 2020.

(60) Provisional application No. 62/816,145, filed on Mar. 10, 2019.

(51) Int. Cl.
| | |
|---|---|
| *G01N 33/48* | (2006.01) |
| *G01N 33/50* | (2006.01) |
| *G16B 30/10* | (2019.01) |
| *G16B 40/00* | (2019.01) |
| *G06N 3/04* | (2006.01) |
| *G06N 3/08* | (2006.01) |
| *G16B 40/20* | (2019.01) |
| *G16B 5/00* | (2019.01) |

(52) U.S. Cl.
CPC ............ *G16B 30/10* (2019.02); *G06N 3/0454* (2013.01); *G06N 3/08* (2013.01); *G16B 5/00* (2019.02); *G16B 40/00* (2019.02); *G16B 40/20* (2019.02)

(58) Field of Classification Search
CPC .......... G16B 30/10; G16B 5/00; G16B 40/00; G16B 40/20; G16B 30/20; G06N 3/0454; G06N 3/08
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |

(Continued)

FOREIGN PATENT DOCUMENTS

| | | |
|---|---|---|
| CN | 105980578 B | 2/2020 |
| WO | WO-2008009751 A3 | 7/2008 |

(Continued)

OTHER PUBLICATIONS

Adessi et al. Solid phase DNA amplification: Charcterisation of primer attachment and amplification mechanisms, Nucl. Acids Res, 2000, 28(20):E87.

(Continued)

*Primary Examiner* — Russell S Negin
(74) *Attorney, Agent, or Firm* — Wilson Sonsini Goodrich & Rosati

(57) ABSTRACT

The present disclosure provides methods, systems, and media for accurate and efficient estimation of a genome of a genus.

20 Claims, 17 Drawing Sheets
(3 of 17 Drawing Sheet(s) Filed in Color)

(56) References Cited

U.S. PATENT DOCUMENTS

| | | | |
|---|---|---|---|
| 5,409,811 | A | 4/1995 | Tabor et al. |
| 5,641,658 | A | 6/1997 | Adams et al. |
| 5,674,716 | A | 10/1997 | Tabor et al. |
| 8,772,473 | B2 | 7/2014 | Huang et al. |
| 10,344,328 | B2 | 7/2019 | Barbee et al. |
| 11,107,554 | B2 | 8/2021 | Pratt et al. |
| 11,276,480 | B2 | 3/2022 | Pratt et al. |
| 2006/0136144 | A1 | 6/2006 | Kamentsky |
| 2010/0169026 | A1 | 7/2010 | Sorenson et al. |
| 2014/0121985 | A1 | 5/2014 | Sayood et al. |
| 2014/0228223 | A1 | 8/2014 | Gnirke et al. |
| 2014/0316716 | A1 | 10/2014 | Jiang et al. |
| 2015/0118685 | A1 | 4/2015 | Clark et al. |
| 2017/0044606 | A1 | 2/2017 | Lo et al. |
| 2018/0373832 | A1 | 12/2018 | Sakarya et al. |
| 2019/0078155 | A1 | 3/2019 | Gordon |
| 2019/0147981 | A1 | 5/2019 | Van Rooyen et al. |
| 2020/0097835 | A1 | 3/2020 | Silver et al. |
| 2020/0303039 | A1 | 9/2020 | Pratt et al. |

FOREIGN PATENT DOCUMENTS

| | | | |
|---|---|---|---|
| WO | WO-2017053446 | A2 | 3/2017 |
| WO | WO-2019084158 | A1 | 5/2019 |
| WO | WO-2020185790 | A1 | 9/2020 |
| WO | WO-2020227137 | A1 | 11/2020 |
| WO | WO-2021007495 | A1 | 1/2021 |
| WO | WO-2022056296 | A1 | 3/2022 |

OTHER PUBLICATIONS

Brenner, et al. Gene expression analysis by massively parallel signature sequencing (MPSS) on microbead arrays. Nat Biotechnol. Jun. 2000;18(6):630-4.

Brenner, et al. In vitro cloning of complex mixtures of DNA on microbeads: physical separation of differentially expressed cDNAs. Proc Natl Acad Sci USA. Feb. 15, 2000;97(4):1665-70.

Cohn et al. Enhancer Identification using Transfer and Adversarial Deep Learning of DNA 1-31 Sequences. In: bioRxiv 264200, Feb. 15, 2018.

Co-pending U.S. Application No. 202117395382, inventor Lee; Linda, filed on Aug. 5, 2021.

Dressman, et al. Transforming single DNA molecules into fluorescent magnetic particles for detection and enumeration of genetic variations. Proc Natl Acad Sci USA. 2003;100(15):8817-8822.

Frazer et al. Cross-Species Sequence Comparisons: A Review of Methods and Available 1-31 Resources. In: Genome Res. 2003.

Kretschy et al., Sequence-Dependent Fluorescence of Cy3- and Cy5-Labeled Double-Stranded DNA, Bioconjugate Chem., vol. 27, No. 3, pp. 840-848 (2016).

Lathuiliere et al. A Comprehensive Analysis of Deep Regression. In: Cornell University Library/ 16-20 Computer Science Computer Vision and Pattern Recognition 2018.

Lizardi, et al. Mutation detection and single-molecule counting using isothermal rolling-circle amplification. Nat Genet. Jul. 1998;19(3):225-32.

Mitra, et al. Digital genotyping and haplotyping with polymerase colonies. Proc Natl Acad Sci USA. 2003.100(10):15926-5931.

Mitra et al. Fluorescent in situ sequencing on polymerase colonies, Anal. Biochem, 320:55-65. (2003).

PCT International Search Report and Written Opinion, PCT Application No. PCT/US20/21909, dated Aug. 14, 2020, 12 pages.

Pemov et al. DNA analysis with multiplex microarray-enhanced PCR, Nucl. Acids Res, 2005, 33(2):e11, pp. 1-9.

Reinartz, et al. Massively parallel signature sequencing (MPSS) as a tool for in-depth quantitative gene expression profiling in all organisms. Brief Funct Genomic Proteomic. Feb. 2002;1(1):95-104.

Zakeri et al., Peak Height Pattern in Dichloro-Rhodamine and Energy Transfer Dye Terminator Sequencing, Biotechniques vol. 25 No. 3, pp. 406-414 (1998).

Au et al. Improving PacBio Long Read Accuracy by Short Read Alignment. PLoS ONE 7(10): e46679 (Oct. 4, 2012).

Co-pending U.S. Application No. 202217574260, inventors Pratt; Mark et al., filed on Jan. 12, 2022.

EP18870560.2 Extended European Search Report dated Nov. 12, 2021.

Feng et al., Improving alignment accuracy on homopolymer regions for semiconductor-based sequencing technologies; BMC Genomics, vol. 17, suppl. 7, pp. 87-93 (2016).

Kretschy et al. Sequence-Dependent Fluorescence of Cy3- and Cy5-Labeled Double-Stranded DNA, Bioconjugate Chemistry. 27, (2016): 840-848.

Lederman, R. Homopolymer Length Filters. Technical Report. Yale University, Department of Computer Science, Oct. 25, 2012, Available online at: https://cpsc.yale.edu/research/technical-reports/2012-technical-reports.

Miller, et al., Aggressive assembly of pyrosequencing reads with mates, Bioinformatics, vol. 24, No. 24, Oct. 24, 2008 (Oct. 24, 2008), pp. 2818-2824.

Mitra, Robi D. et al. Fluorescent in situ sequencing on polymerase colonies. Analytical biochemistry vol. 320, 1 (2003): 55-65.

PCT/US2018/057340 International Search Report and Written Opinion dated Feb. 15, 2019.

PCT/US2021/049923 International Search Report and Written Opinion dated Feb. 14, 2022.

Lizardi, P. M. et al. Mutation detection and single-molecule counting using isothermal rolling-circle amplification. Nature genetics vol. 19,3 (1998): 225-32.

Shendure, J. et al. Next-generation DNA sequencing. Nat Biotechnol 26, 1135-1145 (2008).

Tabor, S. et al. A single residue in DNA polymerases of the *Escherichia coli* DNA polymerase I family is critical for distinguishing between deoxy- and dideoxyribonucleotides. Proc. Natl. Acad. Sci. USA, 92:14 (1995) pp. 6339-6343.

Tabor, S. et al. Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.

U.S. Appl. No. 17/090,176 Notice of Allowance dated Jun. 3, 2021.

U.S. Appl. No. 17/406,464 Notice of Allowance dated Dec. 9, 2021.

U.S. Appl. No. 17/090,176 Office Action dated Mar. 9, 2021.

Vineetha, V et al. SPARK-MSNA: Efficient algorithm on Apache Spark for aligning multiple similar DNA/RNA sequences with supervised learning. Scientific reports vol. 9,1 6631. Apr. 29, 2019.

1010

1020

1300

1320

> Retrain a trained algorithm to generate a new or amended model

1330

> Replace a model

Use different estimation models for a plurality of organisms

METHODS AND SYSTEMS FOR SEQUENCE CALLING

CROSS-REFERENCE

This application is a continuation of International Application No. PCT/US2020/021909, filed Mar. 10, 2020, which claims the benefit of U.S. Patent Application No. 62/816,145, filed Mar. 10, 2019, each of which is incorporated by reference herein in its entirety.

BACKGROUND

The goal to elucidate the entire human genome has created interest in technologies for rapid nucleic acid (e.g., DNA) sequencing, both for small and large scale applications. As knowledge of the genetic basis for human diseases increases, high-throughput DNA sequencing has been leveraged for myriad clinical applications. Despite the prevalence of nucleic acid sequencing methods and systems in a wide range of molecular biology and diagnostics applications, such methods and systems may encounter challenges in accurate base calling, such as when sequencing signals include regions of repeating nucleotide bases called homopolymers. In particular, sequencing methods that perform base calling based on quantified characteristic signals indicating nucleotide incorporation can have sequencing errors (e.g., in quantifying homopolymer lengths), stemming from random and unpredictable systematic variations in signal levels and context dependent signals that may be different for every sequence. Such signal variations and context dependency signals may cause issues with sequence (e.g., homopolymer) calling.

SUMMARY

Recognized herein is a need for improved base calling of sequences, such as sequences containing homopolymers. Methods and systems provided herein can significantly reduce or eliminate errors in quantifying homopolymer lengths and errors associated with context dependence. Such methods and systems may achieve accurate and efficient base calling of sequences (such as sequences containing homopolymers), quantification of homopolymer lengths, and quantification of context dependency in sequence signals.

In an aspect, the present disclosure provides a method for generating a training set, the method comprising: obtaining a first trained algorithm comprising a first mapping between actual reference sequencing signals and trusted reference sequencing signals, wherein the actual reference sequencing signals and the trusted reference sequencing signals represent parts of a reference genome of a first genus that differs from a second genome of a second genus, wherein the reference genome is smaller than the second genome; obtaining actual sequencing signals corresponding to the second genome; and generating a training set for training a second trained algorithm comprising a second mapping between actual sequencing signals corresponding to the second genome and trusted sequencing signals corresponding to the second genome, wherein the training set is generated based on the first mapping with the actual sequencing signals corresponding to the second genome.

In some embodiments, the first trained algorithm differs from the second trained algorithm. In some embodiments, the first trained algorithm is identical to the second trained algorithm. In some embodiments, generating the first mapping comprises training a first neural network. In some embodiments, the second genome is the human genome.

In another aspect, the present disclosure provides a method for generating a training set, the method comprising: training a first neural network to generate a first mapping between actual reference sequencing signals to trusted reference sequencing signals, wherein the actual reference sequencing signals and the trusted reference sequencing signals represent parts of a reference genome that differs from a human genome and is smaller than the human genome; receiving or generating actual human sequencing signals; and generating a human training set for training a second neural network to provide a second mapping between actual human sequencing signals to trusted human sequencing signals, wherein generating the human training set is based on the first mapping, and comprises feeding the second neural network with the actual human sequencing signals.

In some embodiments, the first neural network differs from the second neural network. In some embodiments, the first neural network is identical to the second neural network. In some embodiments, the method further comprises training the second neural network, using the human training set, to map the actual human sequencing signals to the trusted human sequencing signals. In some embodiments, generating the human training set comprises aligning the actual human sequencing signals to trusted reference sequencing signals that represent the entire reference genome. In some embodiments, training the first neural network comprises aligning the actual reference sequencing signals to trusted reference sequencing signals that represent the entire reference genome. In some embodiments, training of the first neural network comprises aligning, using a first alignment process, the actual reference sequencing signals to trusted reference sequencing signals that represent the entire reference genome; and wherein generating the human training set comprises aligning, using a second alignment process, the actual human sequencing signals to trusted reference sequencing signals that represent the entire reference genome; wherein the first alignment process is less resource consuming than the second alignment process. In some embodiments, the first alignment process comprises calculating correlations between the actual reference sequencing signals and different parts of the trusted reference sequencing signals that represent the entire reference genome. In some embodiments, the second alignment process comprises using a hash-based search to perform the aligning. In some embodiments, training the first neural network comprises performing one or more iterations of: selecting a portion of the actual reference sequencing signals and a portion of the trusted reference sequencing signals associated with the selected portion of the reference sequencing signals; using the first neural network to process the selected portion of the actual reference sequencing signals to produce first neural network output signals; calculating an error that represents a difference between the first neural network output signals and the selected portion of the trusted reference sequencing signals; and adjusting the first neural network by backpropagating the error. In some embodiments, the first neural network is a regression network. In some embodiments, the regression network is a fully connected regression network. In some embodiments, the regression network comprises an input layer that comprises one neuron per value of the actual reference signals. In some embodiments, the regression network comprises a plurality of intermediate layers that are larger than the input layer. In some embodiments, the regression network comprises an input layer comprising about one hundred neurons, an output layer comprising about one hundred neurons, and a plurality of intermediate layers each comprising about eight hundred neurons. In some embodiments, generating the human training set comprises aligning truncated actual human sequencing signals to truncated trusted reference sequencing signals that represent the entire reference genome. In some embodiments, the method further comprises using the second neural network to process the actual human sequencing signals and additional information of a type that differs from the actual human sequencing signals. In some embodiments, the additional information comprises information regarding photometry background noise. In some embodiments, the additional information comprises sequencing signals obtained from the preamble. In some embodiments, the additional information comprises local information corresponding to the vicinity of the readings. In some embodiments, the additional information comprises flow information indicative of at least one out of a flow base and a flow position.

In another aspect, the present disclosure provides a method for first genus-based estimation of a genome of a second genus, the method comprising: for each of a plurality of parts of the genome of the second genus: receiving or generating actual sequencing signals that represent the part of genome of the second genus; and estimating the part of the genome of the second genus based on the actual sequencing signals; wherein the estimating comprises applying a second machine learning process to the actual sequencing signals; wherein the second machine learning process is trained to provide a second mapping between actual sequencing signals corresponding to the second genome to trusted sequencing signals corresponding to the second genome; wherein the second mapping is generated based on a first mapping between actual reference sequencing signals to trusted reference sequencing signals; and wherein the actual reference sequencing signals and the trusted reference sequencing signals represent parts of a reference genome of the first genus that differs from a second genus comprising a second genome, wherein the reference genome is smaller than the second genome.

In some embodiments, the method further comprises generating the first mapping by training a first neural network. In some embodiments, the second genome is the human genome. In some embodiments, estimating the part of the human genome comprises calculating a confidence level for at least one estimated nucleotide of the part of the human genome. In some embodiments, the method further comprises determining a validity of the actual human sequencing signals based on confidence levels associated with the at least one estimated nucleotide.

In another aspect, the present disclosure provides a method for estimating a genome of a genus, the method comprising: (a) receiving or generating actual sequencing signals that represent a first part of the genome of the genus; (b) applying a current model on at least a portion of the actual sequencing signals to provide partial current results; wherein the current model is generated by a trained algorithm; (c) evaluating an accuracy of the partial current results; (d) determining, based on the accuracy of the partial current results, whether to continue using the current model for completing the estimation of the genome; (e) upon determining to continue using the current model, completing the estimation of the genome using the current model; and (f) upon determining not to continue using the current model, obtaining a second model having sufficient accuracy, and estimating the genome using the second model.

In some embodiments, the model is generated based on information corresponding to a reference genome that is smaller than the genome of the genus. In some embodiments, the estimation is executed by a computer system, and wherein at least one model that was used by the computer system prior to using the current model is generated based on information corresponding to a reference genome that is smaller than the genome of the genus. In some embodiments, the method further comprises executing a plurality of iterations of (a)-(f).

In another aspect, the present disclosure provides a computer-implemented method for estimating genomes of a plurality of organisms of a genus, the method comprising: performing a plurality of different estimation processes for estimating the genomes of the plurality of organisms, wherein performing the plurality of different estimation processes comprises using a plurality of different estimation models.

In some embodiments, at least one of the plurality of different models is generated by retraining a trained algorithm. In some embodiments, the retraining is performed based, at least in part, on information corresponding to a reference genome that is smaller than the genome of the genus. In some embodiments, at least one of the plurality of different models is generated based on information corresponding to a reference genome that is smaller than the genome of the genus. In some embodiments, the method further comprises replacing a model of the plurality of different models by a second model during each of a plurality of predefined durations of time. In some embodiments, the method further comprises replacing a model of the plurality of different models by a second model during each of a plurality of predefined numbers of estimation processes. In some embodiments, the method further comprises replacing a model of the plurality of different models by a second model based on an evaluation of an accuracy of the model.

In another aspect, the present disclosure provides a method for estimating a genome of a genus, the method comprising: estimating the genome of the genus, wherein the estimating comprises selecting a model from among a plurality of different models, and using the selected model to estimate the genome of the genus.

In some embodiments, the selecting is based on an estimate regarding an accuracy of the estimation corresponding to the plurality of models. In some embodiments, the estimate is based on tests made on parts of the genome. In some embodiments, the estimating is performed by a computer system.

In another aspect, the present disclosure provides a computer-implemented method for estimating a genome of a genus, the method comprising: receiving or generating actual sequencing signals that represent at least a part of the genome of the genus; wherein the actual sequencing signals are generated by imaging a substrate comprising a plurality of substrate segments; and estimating the genome of the genus by applying a first module to signals from among the actual sequencing signals associated with a first substrate segment of the plurality of substrate segments and applying a second module that differs from the first module to signals from among the actual sequencing signals associated with a second substrate segment of the plurality of substrate segments.

In some embodiments, the plurality of substrate segments are determined based on expected or actual differences between an illumination of the plurality of substrate segments. In some embodiments, the plurality of substrate segments are determined based on expected or actual differences between a collection or measurement of radiation from the plurality of substrate segments. In some embodiments, the plurality of substrate segments are determined based on expected or actual distribution of chemical materials over the plurality of substrate segments. In some embodiments, the plurality of substrate segments comprise a same shape and/or size. In some embodiments, at least two of the plurality of substrate segments differ by at least one shape and size.

In another aspect, the present disclosure provides a computer-implemented method for estimating a genome of a genus, the method comprising: receiving or generating actual sequencing signals that represent at least a part of the genome of the genus, wherein the actual sequencing signals belong to at least one image of at least one part of a substrate that is linked to multiple DNA beads; and estimating the genome of the genus by applying at least one model to the actual sequencing signals.

Another aspect of the present disclosure provides a non-transitory computer-readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 13 shows an example of a method for estimating genomes of a plurality of organisms of a genus;

DETAILED DESCRIPTION

Figure 1:
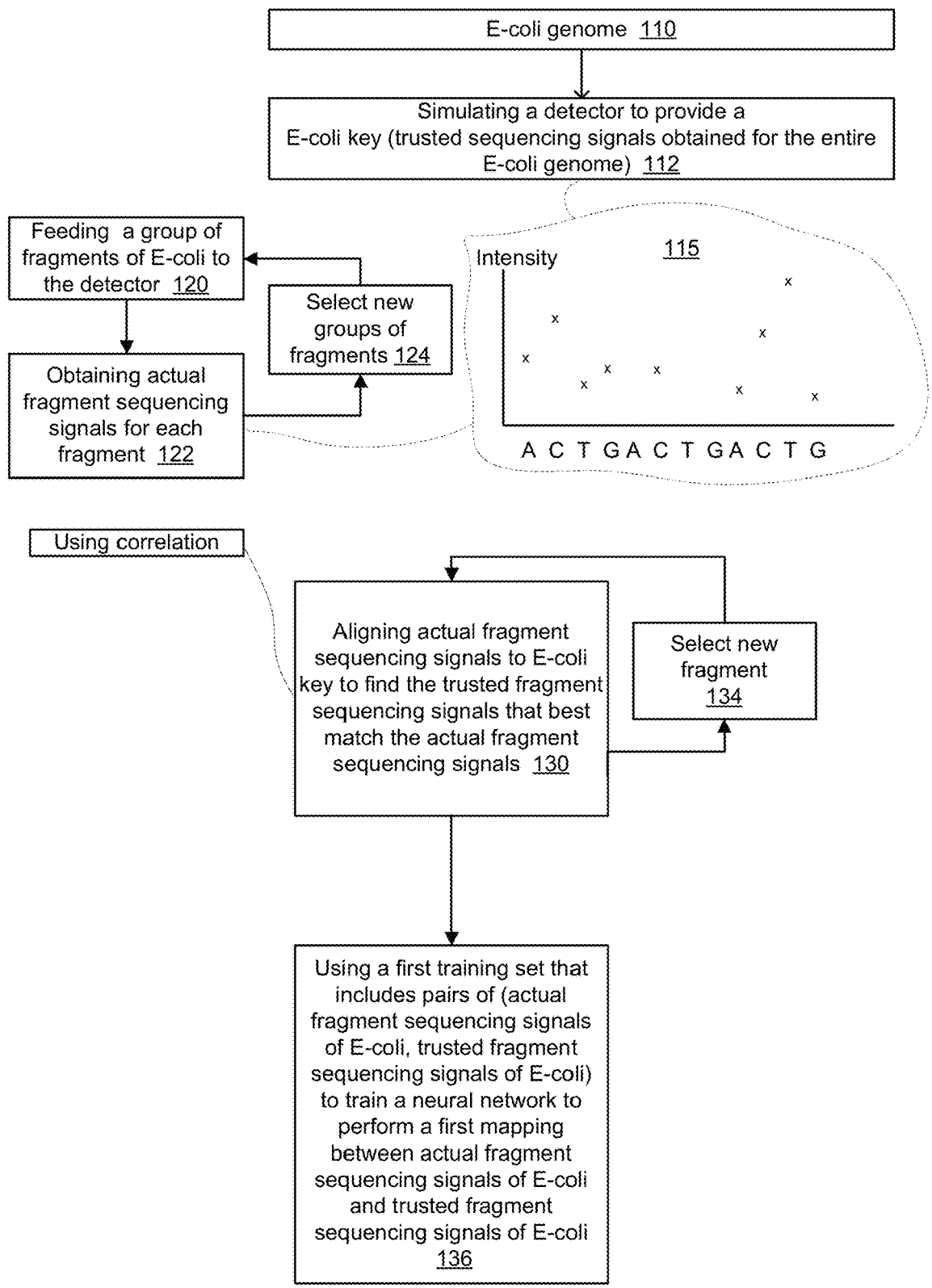
FIG. 1 shows an example of a method 100 for training a neural network to perform a first mapping between actual fragment sequencing signals of E. coli and trusted fragment sequencing signals of E. coli.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used in the specification and claims, the singular form "a", "an", and "the" include plural references unless the context clearly dictates otherwise.

The term "at least partially" as used herein, generally refers to any fraction of a whole amount. For example, "at least partially" may refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99.9%, or more of a whole amount.

The term "sequencing," as used herein, generally refers to a process for generating or identifying a sequence of a biological molecule, such as a nucleic acid molecule or a polypeptide. Such sequence may be a nucleic acid sequence, which may include a sequence of nucleic acid bases (e.g., nucleobases). Sequencing methods may be massively parallel array sequencing (e.g., Illumina sequencing), which may be performed using template nucleic acid molecules immobilized on a support, such as a flow cell or beads. Sequencing methods may include, but are not limited to: high-throughput sequencing, next-generation sequencing, sequencing-by-synthesis, flow sequencing, massively-parallel sequencing, shotgun sequencing, single-molecule sequencing, nanopore sequencing, pyrosequencing, semiconductor sequencing, sequencing-by-ligation, sequencing-by-hybridization, RNA-Seq (Illumina), Digital Gene Expression (Helicos), Single Molecule Sequencing by Synthesis (SMSS) (Helicos), Clonal Single Molecule Array (Solexa), and Maxim-Gilbert sequencing.

The term "flow sequencing," as used herein, generally refers to a sequencing-by-synthesis (SBS) process in which cyclic or acyclic introduction of single nucleotide solutions produce discrete DNA extensions that are sensed (e.g., by a detector that detects fluorescence signals from the DNA extensions).

The term "read," as used herein, generally refers to a nucleic acid sequence, such as a sequencing read. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

The term "subject," as used herein, generally refers to an individual or entity from which a biological sample (e.g., a biological sample that is undergoing or will undergo processing or analysis) may be derived. A subject may be an animal (e.g., mammal or non-mammal) or plant. The subject may be a human, dog, cat, horse, pig, bird, non-human primate, simian, farm animal, companion animal, sport animal, or rodent. A subject may be a patient. The subject may have or be suspected of having a disease or disorder, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. Alternatively or in addition, a subject may be known to have previously have a disease or disorder. The subject may have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease. A subject may be undergoing treatment for a disease or disorder. A subject may be symptomatic or asymptomatic of a given disease or disorder. A subject may be healthy (e.g., not suspected of having disease or disorder). A subject may have one or more risk factors for a given disease. A subject may have a given weight, height, body mass index, or other physical characteristic. A subject may have a given ethnic or racial heritage, place of birth or residence, nationality, disease or remission state, family medical history, or other characteristic.

The term "sample," as used herein, generally refers to a biological sample. As used herein, the term "biological sample" generally refers to a sample obtained from a subject. The biological sample may be obtained directly or indirectly from the subject. A sample may be obtained from a subject via any suitable method, including, but not limited to, spitting, swabbing, blood draw, biopsy, obtaining excretions (e.g., urine, stool, sputum, vomit, or saliva), excision, scraping, and puncture. A sample may be obtained from a subject by, for example, intravenously or intraarterially accessing the circulatory system, collecting a secreted biological sample (e.g., stool, urine, saliva, sputum, etc.), breathing, or surgically extracting a tissue (e.g., biopsy). The sample may be obtained by non-invasive methods including but not limited to: scraping of the skin or cervix, swabbing of the cheek, or collection of saliva, urine, feces, menses, tears, or semen. Alternatively, the sample may be obtained by an invasive procedure such as biopsy, needle aspiration, or phlebotomy. A sample may comprise a bodily fluid such as, but not limited to, blood (e.g., whole blood, red blood cells, leukocytes or white blood cells, platelets), plasma, serum, sweat, tears, saliva, sputum, urine, semen, mucus, synovial fluid, breast milk, colostrum, amniotic fluid, bile, bone marrow, interstitial or extracellular fluid, or cerebrospinal fluid. For example, a sample may be obtained by a puncture method to obtain a bodily fluid comprising blood and/or plasma. Such a sample may comprise both cells and cell-free nucleic acid material. Alternatively, the sample may be obtained from any other source including but not limited to blood, sweat, hair follicle, buccal tissue, tears, menses, feces, or saliva. The biological sample may be a tissue sample, such as a tumor biopsy. The sample may be obtained from any of the tissues provided herein including, but not limited to, skin, heart, lung, kidney, breast, pancreas, liver, intestine, brain, prostate, esophagus, muscle, smooth muscle, bladder, gall bladder, colon, or thyroid. The methods of obtaining provided herein include methods of biopsy including fine needle aspiration, core needle biopsy, vacuum assisted biopsy, large core biopsy, incisional biopsy, excisional biopsy, punch biopsy, shave biopsy or skin biopsy. The biological sample may comprise one or more cells. A biological sample may comprise one or more nucleic acid molecules such as one or more deoxyribonucleic acid (DNA) and/or ribonucleic acid (RNA) molecules (e.g., included within cells or not included within cells). Nucleic acid molecules may be included within cells. Alternatively or in addition, nucleic acid molecules may not be included within cells (e.g., cell-free nucleic acid molecules). The biological sample may be a cell-free sample.

The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition to, cell-free nucleic acid molecules may be released into bodily fluids from healthy cells.

A biological sample may be obtained directly from a subject and analyzed without any intervening processing, such as, for example, sample purification or extraction. For example, a blood sample may be obtained directly from a subject by accessing the subject's circulatory system, removing the blood from the subject (e.g., via a needle), and transferring the removed blood into a receptacle. The receptacle may comprise reagents (e.g., anti-coagulants) such that the blood sample is useful for further analysis. Such reagents may be used to process the sample or analytes derived from the sample in the receptacle or another receptacle prior to analysis. In another example, a swab may be used to access epithelial cells on an oropharyngeal surface of the subject. Following obtaining the biological sample from the subject, the swab containing the biological sample may be contacted with a fluid (e.g., a buffer) to collect the biological fluid from the swab.

Any suitable biological sample that comprises one or more nucleic acid molecules may be obtained from a subject. A sample (e.g., a biological sample or cell-free biological sample) suitable for use according to the methods provided herein may be any material comprising tissues, cells, degraded cells, nucleic acids, genes, gene fragments, expression products, gene expression products, and/or gene expression product fragments of an individual to be tested. A biological sample may be solid matter (e.g., biological tissue) or may be a fluid (e.g., a biological fluid). In general, a biological fluid may include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. Methods for determining sample suitability and/or adequacy are provided. A sample may include, but is not limited to, blood, plasma, tissue, cells, degraded cells, cell-free nucleic acid molecules, and/or biological material from cells or derived from cells of an individual such as cell-free nucleic acid molecules. The sample may be a heterogeneous or homogeneous population of cells, tissues, or cell-free biological material. The biological sample may be obtained using any method that can provide a sample suitable for the analytical methods described herein.

A sample (e.g., a biological sample or cell-free biological sample) may undergo one or more processes in preparation for analysis, including, but not limited to, filtration, centrifugation, selective precipitation, permeabilization, isolation, agitation, heating, purification, and/or other processes. For example, a sample may be filtered to remove contaminants or other materials. In an example, a sample comprising cells may be processed to separate the cells from other material in the sample. Such a process may be used to prepare a sample comprising only cell-free nucleic acid molecules. Such a process may consist of a multi-step centrifugation process. Multiple samples, such as multiple samples from the same subject (e.g., obtained in the same or different manners from the same or different bodily locations, and/or obtained at the same or different times (e.g., seconds, minutes, hours, days, weeks, months, or years apart)) or multiple samples from different subjects may be obtained for analysis as described herein. In an example, the first sample is obtained from a subject before the subject undergoes a treatment regimen or procedure and the second sample is obtained from the subject after the subject undergoes the treatment regimen or procedure. Alternatively or in addition to, multiple samples may be obtained from the same subject at the same or approximately the same time. Different samples obtained from the same subject may be obtained in the same or different manner. For example, a first sample may be obtained via a biopsy and a second sample may be obtained via a blood draw. Samples obtained in different manners may be obtained by different medical professionals, using different techniques, at different times, and/or at different locations. Different samples obtained from the same subject may be obtained from different areas of a body. For example, a first sample may be obtained from a first area of a body (e.g., a first tissue) and a second sample may be obtained from a second area of the body (e.g., a second tissue).

A biological sample as used herein (e.g., a biological sample comprising one or more nucleic acid molecules) may not be purified when provided in a reaction vessel. Furthermore, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) molecules of a biological sample may not be extracted from the biological sample when providing the biological sample to a reaction vessel. Moreover, a target nucleic acid (e.g., a target RNA or target DNA molecules) present in a biological sample may not be concentrated when providing the biological sample to a reaction vessel. Alternatively, a biological sample may be purified and/or nucleic acid molecules may be isolated from other materials in the biological sample.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups.

Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double-stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. Nucleic acids may have any three-dimensional structure, and may perform any function, known or unknown. A nucleic acid molecule can have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bio informatics applications such as functional genomics and homology searching. Oligonucleotides may include one or more nonstandard nucleotide(s), nucleotide analog(s), and/or modified nucleotides. Non-limiting examples of nucleic acids include DNA, RNA, genomic DNA (e.g., gDNA such as sheared gDNA), cell-free DNA (e.g., cfDNA), synthetic DNA/RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or following assembly of the nucleic acid. The sequence of nucleotides of a nucleic acid may be interrupted by non-nucleotide components. A nucleic acid may be further modified following polymerization, such as by conjugation or binding with a reporter agent.

A target nucleic acid or sample nucleic acid as described herein may be amplified to generate an amplified product. A target nucleic acid may be a target RNA or a target DNA. When the target nucleic acid is a target RNA, the target RNA may be any type of RNA, including types of RNA described elsewhere herein. The target RNA may be viral RNA and/or tumor RNA. A viral RNA may be pathogenic to a subject. Non-limiting examples of pathogenic viral RNA include human immunodeficiency virus I (HIV I), human immunodeficiency virus n (HIV 11), orthomyxoviruses, Ebola virus. Dengue virus, influenza viruses (e.g., H1N1, H3N2, H7N9, or H5N1), hepesvirus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

A biological sample may comprise a plurality of target nucleic acid molecules. For example, a biological sample may comprise a plurality of target nucleic acid molecules from a single subject. In another example, a biological sample may comprise a first target nucleic acid molecule from a first subject and a second target nucleic acid molecule from a second subject.

As used herein, a "double-stranded" molecule is a molecule comprising a region of double-stranded nucleic acid molecule. In some embodiments, double-stranded is 100% double-stranded. In some embodiments, double-stranded is at least 50, 55, 60, 65, 70, 75, 80, 85, 90, 92, 95, 97, 99 or 100% double stranded. Each possibility represents a separate embodiment of the invention. In some embodiments, a double-stranded molecule comprises a stretch of double-stranded nucleotides that is at least 1, 2, 3, 4, 5, 6, 7, 8, 9, 10, 12, 14, 15, 16, 18, 20, 25, 30, 35, 40, 45 or 50 bases long. Each possibility represents a separate embodiment of the invention. In some embodiments, the double-stranded molecule comprises a single-stranded overhang. In some embodiments, the overhang is not more than 1, 2, 3, 4, 5, 6, 7, 8, 9 or 10 bases is length. Each possibility represents a separate embodiment of the invention.

The term "nucleotide," as used herein, generally refers to a substance including a base (e.g., a nucleobase), sugar moiety, and phosphate moiety. A nucleotide may comprise a free base with attached phosphate groups. A substance including a base with three attached phosphate groups may be referred to as a nucleoside triphosphate. When a nucleotide is being added to a growing nucleic acid molecule strand, the formation of a phosphodiester bond between the proximal phosphate of the nucleotide to the growing chain may be accompanied by hydrolysis of a high-energy phosphate bond with release of the two distal phosphates as a pyrophosphate. The nucleotide may be naturally occurring or non-naturally occurring (e.g., a modified or engineered nucleotide).

The term "nucleotide analogs," as used herein, may include, but are not limited to, diaminopurine, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, phosphoroselenoate nucleic acids, and the like. In some cases, nucleotides may include modifications in their phosphate moieties, including modifications to a triphosphate moiety. Additional, non-limiting examples of modifications include phosphate chains of greater length (e.g., a phosphate chain having 4, 5, 6, 7, 8, 9, 10, or more than 10 phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic millimeter (mm), higher safety (e.g., resistance to accidental or purposeful synthesis of natural toxins), easier discrimination in photo-programmed polymerases, or lower secondary structure. Nucleotide analogs may be capable of reacting or bonding with detectable moieties for nucleotide detection. An analog to a cleavable base may be the non-cleavable alternative to the base. For example, thymine is a non-cleavable analog to uracil and adenine is a non-cleavable analog of inosine.

The term "free nucleotide analog" as used herein, generally refers to a nucleotide analog that is not coupled to an additional nucleotide or nucleotide analog. Free nucleotide analogs may be incorporated in to the growing nucleic acid chain by primer extension reactions.

As used herein, the term "primer" or "primer molecule" generally refers to a polynucleotide which is complementary to a portion of a template nucleic acid molecule. For example, a primer may be complementary to a portion of a strand of a template nucleic acid molecule. The primer may be a strand of nucleic acid that serves as a starting point for nucleic acid synthesis, such as a primer extension reaction which may be a component of a nucleic acid reaction (e.g., nucleic acid amplification reaction such as PCR). A primer may hybridize to a template strand and nucleotides (e.g., canonical nucleotides or nucleotide analogs) may then be added to the end(s) of a primer, sometimes with the aid of a polymerizing enzyme such as a polymerase. Thus, during replication of a DNA sample, an enzyme that catalyzes replication may start replication at the 3'-end of a primer attached to the DNA sample and copy the opposite strand. A primer (e.g., oligonucleotide) may have one or more functional groups that may be used to couple the primer to a support or carrier, such as a bead or particle. The length of the primer may be between 8 nucleotide bases to 50 nucleotide bases. The length of the primer may be greater than or equal to 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases, or 50 nucleotide bases.

A primer may be completely or partially complementary to a template nucleic acid. A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid.

The term "% sequence identity" may be used interchangeably herein with the term "% identity" and may refer to the level of nucleotide sequence identity between two or more nucleotide sequences, when aligned using a sequence alignment program. As used herein, 80% identity may be the same thing as 80% sequence identity determined by a defined algorithm, and means that a given sequence is at least 80% identical to another length of another sequence. The % identity may be selected from, e.g., at least 60%, at least 65%, at least 70%, at least 75%, at least 80%, at least 85%, at least 90%, at least 95%, or at least 99% or more sequence identity to a given sequence. The % identity may be in the range of, e.g., about 60% to about 70%, about 70% to about 80%, about 80% to about 85%, about 85% to about 90%, about 90% to about 95%, or about 95% to about 99%.

The terms "% sequence homology" or "percent sequence homology" or "percent sequence identity" may be used interchangeably herein with the terms "% homology," "% sequence identity," or "% identity" and may refer to the level of nucleotide sequence homology between two or more nucleotide sequences, when aligned using a sequence alignment program. For example, as used herein, 80% homology may be the same thing as 80% sequence homology determined by a defined algorithm, and accordingly a homologue of a given sequence has greater than 80% sequence homology over a length of the given sequence. The % homology may be selected from, e.g., at least 60%, at least 65%, at least 70%, at least 75%, at least 80%, at least 85%, at least 90%, at least 95%, or at least 99% or more sequence homology to a given sequence. The % homology may be in the range of, e.g., about 60% to about 70%, about 70% to about 80%, about 80% to about 85%, about 85% to about 90%, about 90% to about 95%, or about 95% to about 99%.

The term "primer extension," as used herein, generally refers to the binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (polymerizing enzymes).

The term "polymerizing enzyme" or "polymerase," as used herein, generally refers to any enzyme capable of catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending the 3' end of an existing nucleotide chain, adding new nucleotides matched to the template strand one at a time via the creation of phosphodiester bonds. The polymerase used herein can have strand displacement activity or non-strand displacement activity. Examples of polymerases include, without limitation, a nucleic acid polymerase. The polymerase can be naturally occurring or synthesized. In some cases, a polymerase has relatively high processivity, namely the capability of the polymerase to consecutively incorporate nucleotides into a nucleic acid template without releasing the nucleic acid template. An example polymerase is a Φ29 polymerase or a derivative thereof. A polymerase can be a polymerization enzyme. In some cases, a transcriptase or a ligase is used (i.e., enzymes which catalyze the formation of a bond). Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase 129 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such, as for example, Sequenase DNA polymerase (ThermoFisher).

A polymerase may be Family A polymerase or a Family B DNA polymerase. Family A polymerases include, for example, Taq, Klenow, and Bst polymerases. Family B polymerases include, for example, Vent(exo-) and Therminator polymerases. Family B polymerases are known to accept more varied nucleotide substrates than Family A polymerases. Family A polymerases are used widely in sequencing by synthesis methods, likely due to their high processivity and fidelity.

The term "complementary sequence," as used herein, generally refers to a sequence that hybridizes to another sequence. Hybridization between two single-stranded nucleic acid molecules may involve the formation of a double-stranded structure that is stable under certain conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "support or "substrate," as used herein, generally refers to a solid or semi-solid support on which reagents such as nucleic acid molecules may be immobilized, such as a slide, a bead, a resin, a chip, an array, a matrix, a membrane, a nanopore, or a gel. Nucleic acid molecules may be synthesized, attached, ligated, or otherwise immobilized. Nucleic acid molecules may be immobilized on a substrate by any method including, but not limited to, physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous, and may have swelling or non-swelling characteristics. A substrate may be shaped to comprise one or more wells, depressions, or other containers, vessels, features, or locations. A plurality of substrates may be configured in an array at various locations. A substrate may be addressable (e.g., for robotic delivery of reagents), or by detection approaches, such as scanning by laser illumination and confocal or deflective light gathering. For example, a substrate may be in optical and/or physical communication with a detector. Alternatively, a substrate may be physically separated from a detector by a distance. An amplification substrate (e.g., a bead) can be placed within or on another substrate (e.g., within a well of a second support) The substrate may have surface properties, such as textures, patterns, microstructure coatings, surfactants, or any combination thereof to retain the amplification substrate (e.g., bead) at a desired location (such as in a position to be in operative communication with a detector). The detector of bead-based supports may be configured to maintain substantially the same read rate independent of the size of the bead. The support may be in optical communication with the detector, may be physically in contact with the detector, may be separated from the detector by a distance, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. The support may be optically coupled to the detector. Immobilization on the support may be aided by an adaptor.

The term "solid support" refers to any artificial solid structure, including any solid support or substrate. Examples of solid supports include, but are not limited to beads, resins, gels, hydrogels, colloids, particles or nanoparticles. For example, a solid support may be a bead. Alternatively, the solid support may be a surface. For example, a solid support may comprise a bead coupled to a surface. Alternatively, the solid support may be a resin. The solid support may be isolatable. The solid support may be tagged. The solid support may be magnetic and isolatable with a magnet. Alternatively or in addition, the solid support may be isolated by centrifugation or some other force that separates by weight, size or some other measurable quantity.

A support (e.g., a solid support) may be or comprise a particle. A particle may be a bead. A bead may comprise any suitable material such as glass or ceramic, one or more polymers, and/or metals. Examples of suitable polymers include, but are not limited to, nylon, polytetrafluoroethylene, polystyrene, polyacrylamide, agarose, cellulose, cellulose derivatives, or dextran. Examples of suitable metals include paramagnetic metals, such as iron. A bead may be magnetic or non-magnetic. For example, a bead may comprise one or more polymers bearing one or more magnetic labels. A magnetic bead may be manipulated (e.g., moved between locations or physically constrained to a given location, e.g., of a reaction vessel such as a flow cell chamber) using electromagnetic forces. A bead may have any useful shape, including, for example, a shape that is approximately cubic, spherical, ellipsoidal, dumbbell-shaped, or any other shape. For example, a bead may be approximately spherical in shape. A bead may have one or more different dimensions including a diameter. A dimension of the bead (e.g., a diameter of the bead) may be less than about 1 mm, less than about 0.1 mm, less than about 0.01 mm, less than about 0.005 mm, less than about 1 nm, less than about 1 µm, or smaller. A dimension of the bead (e.g., a diameter of the bead) may be between about 1 nm to about 100 nm, about 1 µm to about 100 µm, about 1 mm to about 100 mm. A collection of beads may comprise one or more beads having the same or different characteristics. For example, a first bead of a collection of beads may have a first diameter and a second bead of the collection of beads may have a second diameter. The first diameter may be the same or approximately the same as or different from the second diameter. Similarly, the first bead may have the same or a different shape and composition than a second bead.

The term "label," as used herein, generally refers to a moiety that is capable of coupling with a species, such as, for example, a nucleotide analog. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after the primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase, or protease).

In some cases, the label may be optically active (e.g., luminescent, e.g., fluorescent or phosphorescent). In some embodiments, an optically-active label is an optically-active dye (e.g., fluorescent dye). Dyes and labels may be incorporated into nucleic acid sequences. Dyes and labels may also be incorporated into linkers, such as linkers for linking one or more beads to one another. For example, labels such as fluorescent moieties may be linked to nucleotides or nucleotide analogs via a linker. Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, propidium iodide, hexidium iodide, dihydroethidium, ethidium homodimer-1 and -2, ethidium monoazide, ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO- 3, PicoGreen, OliGreen, RiboGreen, SYBR Gold, SYBR Green I, SYBR Green II, SYBR DX, SYTO labels (e.g., SYTO-40, -41, -42, -43, -44, and -45 (blue); SYTO-13, -16, -24, -21, -23, -12, -11, -20, -22, -15, -14, and -25 (green); SYTO-81, -80, -82, -83, -84, and-85 (orange); and SYTO-64, -17, -59, -61, -62, -60, and -63 (red)), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor labels (e.g., AlexaFluor 350, 405, 430, 488, 532, 546, 555, 568, 594, 610, 633, 635, 647, 660, 680, 700, 750, and 790 dyes), DyLight labels (e.g., DyLight 350, 405, 488, 550, 594, 633, 650, 680, 755, and 800 dyes), Black Hole Quencher Dyes (Biosearch Technologies) (e.g., BH1-0, BHQ-1, BHQ-3, and BHQ-10), QSY Dye fluorescent quenchers (Molecular Probes/Invitrogen) (e.g., QSY7, QSY9, QSY21, and QSY35), Dabcyl, Dabsyl, CySQ, Cy7Q, Dark Cyanine dyes (GE Healthcare), Dy-Quenchers (Dyomics) (e.g., DYQ-660 and DYQ-661), ATTO fluorescent quenchers (ATTO-TEC GmbH) (e.g., ATTO 540Q, ATTO 580Q, ATTO 612Q, Atto532 [e.g., Atto 532 succinimidyl ester], and Atto633), and other fluorophores and/or quenchers. A fluorescent dye may be excited by application of energy corresponding to the visible region of the electromagnetic spectrum (e.g., between about 430-770 nanometers (nm)). Excitation may be done using any useful apparatus, such as a laser and/or light emitting diode. Optical elements including, but not limited to, mirrors, waveplates, filters, monochromaters, gratings, beam splitters, and lenses may be used to direct light to or from a fluorescent dye. A fluorescent dye may emit light (e.g., fluoresce) in the visible region of the electromagnetic spectrum ((e.g., between about 430-770 nm). A fluorescent dye may be excited over a single wavelength or a range of wavelengths. A fluorescent dye may be excitable by light in the red region of the visible portion of the electromagnetic spectrum (about 625-740 nm) (e.g., have an excitation maximum in the red region of the visible portion of the electromagnetic spectrum). Alternatively or in addition to, fluorescent dye may be excitable by light in the green region of the visible portion of the electromagnetic spectrum (about 500-565 nm) (e.g., have an excitation maximum in the green region of the visible portion of the electromagnetic spectrum). A fluorescent dye may emit signal in the red region of the visible portion of the electromagnetic spectrum (about 625-740 nm) (e.g., have an emission maximum in the red region of the visible portion of the electromagnetic spectrum). Alternatively or in addition to, fluorescent dye may emit signal in the green region of the visible portion of the electromagnetic spectrum (about 500-565 nm) (e.g., have an emission maximum in the green region of the visible portion of the electromagnetic spectrum).

In some examples, labels may be nucleic acid intercalator dyes. Examples include, but are not limited to ethidium bromide, YOYO-1, SYBR Green, and EvaGreen. The near-field interactions between energy donors and energy acceptors, between intercalators and energy donors, or between intercalators and energy acceptors can result in the generation of unique signals or a change in the signal amplitude. For example, such interactions can result in quenching (i.e., energy transfer from donor to acceptor that results in non-radiative energy decay) or Forster resonance energy transfer (FRET) (i.e., energy transfer from the donor to an acceptor that results in radiative energy decay). Other examples of labels include electrochemical labels, electrostatic labels, colorimetric labels and mass tags.

Labels may be quencher molecules. The term "quencher," as used herein, refers to a molecule that may be energy acceptors. A quencher may be a molecule that can reduce an emitted signal. For example, a template nucleic acid molecule may be designed to emit a detectable signal. Incorporation of a nucleotide or nucleotide analog comprising a quencher can reduce or eliminate the signal, which reduction or elimination is then detected. Luminescence from labels (e.g., fluorescent moieties, such as fluorescent moieties linked to nucleotides or nucleotide analogs) may also be quenched (e.g., by incorporation of other nucleotides that may or may not comprise labels). In some cases, as described elsewhere herein, labeling with a quencher can occur after nucleotide or nucleotide analog incorporation. In some cases, the label may be a type that does not self-quench or exhibit proximity quenching. Non-limiting examples of a label type that does not self-quench or exhibit proximity quenching include Bimane derivatives such as Monobromobimane. The term "proximity quenching," as used herein, generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nm to 50 nm of each other. Examples of quenchers include, but are not limited to, Black Hole Quencher Dyes (Biosearch Technologies) (e.g., BH1-0, BHQ-1, BHQ-3, and BHQ-10), QSY Dye fluorescent quenchers (Molecular Probes/Invitrogen) (e.g., QSY7, QSY9, QSY21, and QSY35), Dabcyl, Dabsyl, Cy5Q, Cy7Q, Dark Cyanine dyes (GE Healthcare), Dy-Quenchers (Dyomics) (e.g., DYQ-660 and DYQ-661), and ATTO fluorescent quenchers (ATTO-TEC GmbH) (e.g., ATTO 540Q, ATTO 580Q, and ATTO 612Q). Fluorophore donor molecules may be used in conjunction with a quencher. Examples of fluorophore donor molecules that can be used in conjunction with quenchers include, but are not limited to, fluorophores such as Cy3B, Cy3, or Cy5; Dy-Quenchers (Dyomics) (e.g., DYQ-660 and DYQ-661); and ATTO fluorescent quenchers (ATTO-TEC GmbH) (e.g., ATTO 540Q, 580Q, and 612Q).

The term "detector," as used herein, generally refers to a device that is capable of detecting a signal, including a signal indicative of the presence or absence of an incorporated nucleotide or nucleotide analog. In some cases, a detector can include optical and/or electronic components that can detect signals. The term "detector" may be used in detection methods. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "adapter" or "adaptor," as used herein, generally refers to a molecule (e.g., polynucleotide) that is adapted to permit a sequencing instrument to sequence a target polynucleotide, such as by interacting with a target nucleic acid molecule to facilitate sequencing (e.g., next generation sequencing (NGS)). The sequencing adapter may permit the target nucleic acid molecule to be sequenced by the sequencing instrument. For instance, the sequencing adapter may comprise a nucleotide sequence that hybridizes or binds to a capture polynucleotide attached to a solid support of a sequencing system, such as a bead or a flow cell. The sequencing adapter may comprise a nucleotide sequence that hybridizes or binds to a polynucleotide to generate a hairpin loop, which permits the target polynucleotide to be sequenced by a sequencing system. The sequencing adapter may include a sequencer motif, which may be a nucleotide sequence that is complementary to a flow cell sequence of another molecule (e.g., a polynucleotide) and usable by the sequencing system to sequence the target polynucleotide. The sequencer motif may also include a primer sequence for use in sequencing, such as sequencing by synthesis. The sequencer motif may include the sequence(s) for coupling a library adapter to a sequencing system and sequence the target polynucleotide (e.g., a sample nucleic acid). An adapter may comprise a barcode.

The term "barcode" or "barcode sequence," as used herein, generally refers to one or more nucleotide sequences that may be used to identify one or more particular nucleic acids (e.g., based on their association with a particular sample, derivation from a particular source such as a particular cell, inclusion in a particular partition or other compartment, etc.). A barcode may comprise at least 1, 2, 3, 4, 5, 6, 7, 8, 9, 10, 11, 12, 13, 14, 15, 16, 17, 18, 19, 20, or more nucleotides (e.g., consecutive nucleotides). A barcode may comprise at least about 10, about 20, about 30, about 40, about 50, about 60, about 70, about 80, about 90, about 100 or more consecutive nucleotides. All of the barcodes used for an amplification and/or sequencing process (e.g., NGS) may be different. The diversity of different barcodes in a population of nucleic acids comprising barcodes may be randomly generated or non-randomly generated. For example, barcode sequences comprising multiple segments maybe assembled in a combinatorial fashion according to a split-pool scheme, in which a plurality of different first segments are distributed amongst a plurality of first partitions, the contents which are then pooled and distributed amongst a plurality of second partitions.

As described herein, the use of barcodes may permit high-throughput analysis of multiple samples using next generation sequencing techniques. A sample comprising a plurality of nucleic acid molecules may be distributed throughout a plurality of partitions (e.g., droplets in an emulsion), where each partition comprises a nucleic acid barcode molecule comprising a unique barcode sequence. The sample may be partitioned such that all or a majority of the partitions of the plurality of partitions include at least one nucleic acid molecule of the plurality of nucleic acid molecules. A nucleic acid molecule and nucleic acid barcode molecule of a given partition may then be used to generate one or more copies and/or complements of at least a sequence of the nucleic acid molecule (e.g., via nucleic acid amplification reactions), which copies and/or complements comprise the barcode sequence of the nucleic acid barcode molecule or a complement thereof. The contents of the various partitions (e.g., amplification products or derivatives thereof) may then be pooled and subjected to sequencing. In some cases, nucleic acid barcode molecules may be coupled to beads. In such cases, the copies and/or complements may also be coupled to the beads. Nucleic acid barcode molecules, and copies and/or complements may be released from the beads within the partitions or after pooling to facilitate nucleic acid sequencing using a sequencing instrument. Because copies and/or complements of the nucleic acid molecules of the plurality of nucleic acid molecules each include a unique barcode sequence or complement thereof, sequencing reads obtained using a nucleic acid sequencing assay may be associated with the nucleic acid molecule of the plurality of nucleic acid molecules to which they correspond. This method may be applied to nucleic acid molecules included within cells divided amongst a plurality of partitions, and/or nucleic acid molecules deriving from a plurality of different samples.

The terms "signal," "signal sequence," and "sequence signal," as used herein, generally refer to a series of signals (e.g., fluorescence measurements) associated with a DNA molecule or clonal population of DNA, comprising primary data. Such signals may be obtained using a high-throughput sequencing technology (e.g., flow SBS). Such signals may be processed to obtain imputed sequences (e.g., during primary analysis).

The terms "sequence" or "sequence read," as used herein, generally refer to a series of nucleotide assignments (e.g, by base calling) made during a sequencing process. Such sequences may be derived from signal sequences (e.g., during primary analysis).

The term "homopolymer," as used herein, generally refers to a polymer or a portion of a polymer comprising identical monomer units, such as a sequence of 0, 1, 2, . . . , N sequential nucleotides. For example, a homopolymer containing sequential A nucleotides may be represented as A, AA, AAA, . . . , up to N sequential A nucleotides. A homopolymer may have a homopolymer sequence. A nucleic acid homopolymer may refer to a polynucleotide or an oligonucleotide comprising consecutive repetitions of a same nucleotide or any nucleotide variants thereof. For example, a homopolymer can be poly(dA), poly(dT), poly (dG), poly(dC), poly(rA), poly(U), poly(rG), or poly(rC). A homopolymer can be of any length. For example, the homopolymer can have a length of at least 2, 3, 4, 5, 10, 20, 30, 40, 50, 100, 200, 300, 400, 500, or more nucleic acid bases. The homopolymer can have from 10 to 500, or 15 to 200, or 20 to 150 nucleic acid bases. The homopolymer can have a length of at most 500, 400, 300, 200, 100, 50, 40, 30, 20, 10, 5, 4, 3, or 2 nucleic acid bases. A molecule, such as a nucleic acid molecule, can include one or more homopolymer portions and one or more non-homopolymer portions. The molecule may be entirely formed of a homopolymer, multiple homopolymers, or a combination of homopolymers and non-homopolymers. In nucleic acid sequencing, multiple nucleotides can be incorporated into a homopolymeric region of a nucleic acid strand. Such nucleotides may be non-terminated to permit incorporation of consecutive nucleotides (e.g., during a single nucleotide flow).

The term "HpN truncation," as used herein, generally refers to a method of processing a set of one or more sequences such that each homopolymer of the set of one or more sequences having a length greater than or equal to an integer N is truncated to a homopolymer of length N. For example, HpN truncation of the sequence "AGGGGGT" to 3 bases may result in a truncated sequence of "AGGGT."

The term "analog alignment," as used herein, generally refers to alignment of signal sequences to a reference signal sequence.

The terms "amplifying," "amplification," and "nucleic acid amplification" are used interchangeably and, as used herein, generally refer to the production of copies of a nucleic acid molecule. For example, "amplification" of DNA generally refers to generating one or more copies of a DNA molecule. An amplicon may be a single-stranded or double-stranded nucleic acid molecule that is generated by an amplification procedure from a starting template nucleic acid molecule. Such an amplification procedure may include one or more cycles of an extension or ligation procedure. The amplicon may comprise a nucleic acid strand, of which at least a portion may be substantially identical or substantially complementary to at least a portion of the starting template. Where the starting template is a double-stranded nucleic acid molecule, an amplicon may comprise a nucleic acid strand that is substantially identical to at least a portion of one strand and is substantially complementary to at least a portion of either strand. The amplicon can be single-stranded or double-stranded irrespective of whether the initial template is single-stranded or double-stranded. Amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). An amplification reaction may be, for example, a polymerase chain reaction (PCR), such as an emulsion polymerase chain reaction (emPCR; e.g., PCR carried out within a microreactor such as a well or droplet). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C.C. PNAS, 1989, 86, 4076-4080 and U.S. Pat. Nos. 5,409,811 and 5,674,716, each of which is herein incorporated by reference in its entirety.

Amplification may be clonal amplification. The term "clonal," as used herein, generally refers to a population of nucleic acids for which a substantial portion (e.g., greater than 50%, 60%, 70%, 80%, 90%, 95%, or 99%) of its members have substantially identical sequences (e.g., have sequences that are at least about 50%, 60%, 70%, 80%, 90%, 95%, or 99% identical to one another). Members of a clonal population of nucleic acid molecules may have sequence homology to one another. Such members may have sequence homology to a template nucleic acid molecule. In some instances, such members may have sequence homology to a complement of the template nucleic acid molecule (e.g., if single stranded). The members of the clonal population may be double stranded or single stranded. Members of a population may not be 100% identical or complementary because, e.g., "errors" may occur during the course of synthesis such that a minority of a given population may not have sequence homology with a majority of the population. For example, at least 50% of the members of a population may be substantially identical to each other or to a reference nucleic acid molecule (i.e., a molecule of defined sequence used as a basis for a sequence comparison). At least 60%, at least 70%, at least 80%, at least 90%, at least 95%, at least 99%, or more of the members of a population may be substantially identical to the reference nucleic acid molecule. Two molecules may be considered substantially identical (or homologous) if the percent identity between the two molecules is at least 60%, 70%, 75%, 80%, 85%, 90%, 95%, 98%, 99%, 99.9% or greater. Two molecules may be considered substantially complementary if the percent complementarity between the two molecules is at least 60%, 70%, 75%, 80%, 85%, 90%, 95%, 98%, 99%, 99.9% or greater. A low or insubstantial level of mixing of non-homologous nucleic acids may occur, and thus a clonal population may contain a minority of diverse nucleic acids (e.g., less than 30%, e.g., less than 10%).

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference). The enhanced signal-to-noise ratio provided by clonal amplification more than outweighs the disadvantages of the cyclic sequencing requirement.

The term "context dependence" or "context dependency," as used herein, generally refers to signal correlations with local sequence, relative nucleotide representation, or genomic locus. Signals for a given sequence may vary due to context dependency, which may depend on the local sequence, relative nucleotide representation of the sequence, or genomic locus of the sequence.

Flow sequencing by synthesis (SBS) may comprise performing repeated DNA extension cycles, wherein individual species of nucleotides and/or labeled analogs are presented to a primer-template-polymerase complex, which then incorporates the nucleotide if complementary. The product of each flow may be measured for each clonal population of templates, e.g., a bead or a colony. The resulting nucleotide incorporations may be detected and quantified by unambiguously distinguishing signals corresponding to or associated with zero, one, two, three, four, five, six, seven, eight, nine, ten, or more than ten sequential incorporations. Accurate quantification of such multiple sequential incorporations comprises quantifying characteristic signals for each possible homopolymer of 0, 1, 2, . . . , N sequential nucleotides incorporated on a colony in each flow. For example, a homopolymer containing sequential A nucleotides may be represented as A, AA, AAA, . . . , up to N sequential A nucleotides. Accurate quantification of homopolymer lengths (e.g., a number of sequential identical nucleotides in a sequence) may encounter challenges owing to random and unpredictable systematic variations in signal level, which can cause errors in quantifying the homopolymer length. In some cases, instrument and detection systematics can be calibrated and removed by monitoring instrument diagnostics and common-mode behavior across large numbers of colonies. Accurate quantification of homopolymer lengths (e.g., a number of sequential identical nucleotides in a sequence) may also encounter challenges owing to sequence context dependent signal, which may be different for every sequence. For example, in the case of fluorescence measurements of dilute labeled nucleotides, sequence context can affect both the number of labeled analogs (variable tolerance for incorporating labeled analogs) as well as fluorescence of individual labeled analogs (e.g., quantum yield of dyes affected by local context of ±5 bases, as described by [Kretschy, et al., Sequence-Dependent Fluorescence of Cy3- and Cy5-Labeled Double-Stranded DNA, *Bioconjugate Chem.*, 27(3), pp. 840-848], which is incorporated herein by reference in its entirety). In practice, with dye-terminator Sanger cycle sequencing, substantial systematic variations in signals have been identified for 3-base contexts (e.g., as described by [Zakeri, et al., Peak height pattern in dichlororhodamine and energy transfer dye terminator sequencing, *Biotechniques*, 25(3), pp. 406-10], which is incorporated herein by reference in its entirety).

Generally, the nomenclature used herein and the laboratory procedures utilized in methods and systems of the present disclosure may include molecular, biochemical, microbiological and recombinant DNA techniques. Details of such techniques may be found in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference.

The term "trusted signal" or "trusted sequencing signal," as used herein, generally refers to a sequencing signal that is an ideal signal, which is error free or at least a signal that is accurate enough to be trusted. The accuracy level may be determined in various manners. In some instances, a trusted signal may be a signal that meets a predetermined threshold for an accuracy level. A trusted sequencing signal may be used as a reference for generating a training set or for training an algorithm (e.g., a classifier such as a machine learning classifier). For example, a trusted sequencing signal may correspond to a known nucleotide sequence (e.g., a sequence of known bases), such that sets of trusted sequencing signals and sets of known nucleotide sequences may be used to construct training sets.

The present disclosure may refer (for simplicity of explanation) to an *E. coli* genome, a human genome, a neural network and shotgun sequencing. These are examples of genomes of different sizes, machine learning processes, and a certain type of sequencing, respectively.

A detector may output actual human fragment sequencing signals that are subject to inaccuracies and noise. These inaccuracies and noise may be difficult or impossible to be analytically calculated in advance, due to their random nature. The present disclosure provides methods and systems that apply machine learning to assist in generating a mapping or classification between input datasets comprising actual human fragment sequencing signals (which may be noisy and inaccurate) and output datasets comprising accurate human fragment sequencing signals. The accurate human fragment sequencing signals may be further processed—for example, be aligned to an accurate human genome, for downstream applications, such as diagnostic and other precision health applications.

The length of the human genome is over three billion base pairs. Therefore, the size of the human genome may present challenges or difficulties in generating, using the human genome only, a direct mapping between a set of actual human fragment sequencing signals (which may be noisy and inaccurate) and a set of accurate human fragment sequencing signals.

The present disclosure provides methods and systems of applying a machine learning process to much smaller genomes—for example on an *E. coli* genome that is about few thousand genes long—in order to provide such a direct mapping between a set of actual human fragment sequencing signals and a set of accurate human fragment sequencing signals. Although the *E. coli* genome differs from the human genome, it may be used during a multiple-phase process that includes one or more of the following: (a) obtaining a first trained algorithm (e.g., machine learning process) comprising a first mapping (e.g., classification or regression) between actual reference sequencing signals and trusted reference sequencing signals; (b) obtaining actual sequencing signals corresponding to the second genome; and (c) generating a training set for training a second trained algorithm (e.g., machine learning process) comprising a second mapping (e.g., classification or regression) between actual sequencing signals corresponding to the second genome and trusted sequencing signals corresponding to the second genome. In some embodiments, the actual reference sequencing signals and the trusted reference sequencing signals represent parts of a reference genome of a first genus that differs from a second genome of a second genus. In some embodiments, the reference genome is smaller than the second genome. In some embodiments, the training set is generated based on the first mapping with the actual sequencing signals corresponding to the second genome.

This multi-phase process generates the second mapping using one or more machine learning processes that are of reasonable complexity and cost.

It will be appreciated that while the present disclosure is explained with respect to correlating and/or mapping, for example, the human genome and *E. coli* genome with various training algorithms, the methods and systems of the present disclosure may be applicable to any two genomes, such as where one genome is bigger and/or more complex than the other genome. For example, actual sequencing signals of a non-human sample may be received or generated.

The present disclosure provides systems, methods, and computer-readable media that generate a second mapping based on a first mapping corresponding to a genus having a genome that is smaller than the human genome. The second mapping can be used to process actual human fragment sequencing signals to produce accurate human fragment sequencing signals, which may be aligned to a reference human genome in order to provide an estimate of the genome of a subject.

The method may comprise obtaining or generating a first trained algorithm comprising a first mapping between reference actual sequencing signals and reference trusted sequencing signals (e.g., between actual *E. coli* fragment sequencing signals and accurate *E. coli* fragment sequencing signals). The second trained algorithm configured to apply the second mapping may be trained using a machine learning process.

A machine learning process may comprise (i) using a first trained algorithm (e.g., a first neural network) that is trained to apply the first mapping to process actual *E. coli* fragment sequencing signals to produce accurate *E. coli* fragment sequencing signals, and (ii) using a second trained algorithm (e.g., a second neural network) that is trained to apply the second mapping to process actual human fragment sequencing signals to produce accurate human fragment sequencing signals. The accurate human fragment sequencing signals may then be aligned to a reference human genome (e.g., for further genomic analysis).

The first trained algorithm may generate a training set (e.g., training dataset) that may be used to train a second trained algorithm (e.g., a second neural network) to apply a second mapping between actual sequencing signals and accurate sequencing signals corresponding to a human genome (e.g., between actual human fragment sequencing signals and accurate human fragment sequencing signals).

The systems, methods, and computer-readable media may be highly efficient in terms of memory and/or computational resources, as they are configured to apply machine learning algorithms on the *E. coli* genome—which is much smaller than the human genome. Therefore, such systems, methods, and computer-readable media may advantageously perform sequence calling or base calling with greater accuracy and efficiency, while using less memory and/or computational resources.

FIG. 1 shows an example of a method 100 for training a neural network configured to apply a first mapping between actual fragment sequencing signals of *E. coli* and trusted fragment sequencing signals of *E. coli*. In some embodiments, method 100 may include one or more of operations 110, 112, 120, 122, 124, 130, 134, and 136.

The method 100 may comprise receiving a genome corresponding to a genus or a species (e.g., an *E. coli* genome) that differs from the human genome (as in operation 110). For example, the *E. coli* genome may comprise about 4.6 million base pairs, which is significant smaller than the human genome (which may comprise about 3 billion base pairs). The use of a smaller genome may be advantageous to reduce computational complexity (thereby enabling faster runtimes with less computational resources), which may scale linearly with the size of the genome.

Next, the method 100 may comprise simulating a detector (e.g., especially simulating the response of the detector to the *E. coli* genome)—assuming a substantially error-free process (as in operation 112).

The method 100 may comprise simulating the chemical and/or optical processes executed by the detector (as in operation 112). The outcome of operation 112 may be an *E. coli* key (115) which includes trusted sequencing signals that may be expected to be obtained from the detector (under a substantially error-free detection process) for the entire *E. coli* genome. The *E. coli* key 115 may include intensity values for A, C, T, G elements for the entire *E. coli* genome.

Next, the method 100 may comprise processing a group of fragments of *E. coli* samples using the detector (as in operation 120).

Next, the method 100 may comprise obtaining actual fragment sequencing signals for each segment (as in operation 122).

Next, the method 100 may comprise selecting a new group of fragments (as in operation 124) and proceeding to operation 120. The set of operations 120, 122, and 124 may be repeated or iterated until receiving actual fragment sequencing signals for the entire *E. coli* genome, or until a substantial amount of actual fragment sequencing signals are received.

In some embodiments, operation 122 may comprise (or may be followed by) rejecting actual fragment sequencing signals that may be defective.

For example, while the noise-free fragment sequencing signals may be expected to represent an integer number of homopolymers, the actual fragment sequencing signals may provide a non-integer number of homopolymers. The deviation from the expected integer numbers of homopolymers may be indicative of an error in the actual fragment sequencing signals, and once the error exceeds a predefined threshold, the actual fragment sequencing signals may be ignored and may not be processed in subsequent operations, such as operations 130 and 136. The error may be calculated in various manners, for example, mean squared error, and the like. The predefined threshold may be set in any manner.

Next, the method 100 may comprise aligning actual fragment sequencing signals to the *E. coli* key 115 (as in operation 130). Operation 130 may comprise correlating the actual fragment sequencing signals against the entire *E. coli* key to find the location of the best matching trusted fragment sequencing signals in the *E. coli* key.

Next, the method 100 may comprise selecting a new group of fragments (as in operation 134) and proceeding to operation 130. The set of operations 130 and 134 may be repeated or iterated until finding, for each one of the actual fragment sequencing signals, best matching trusted fragment sequencing signals in the *E. coli* key. In some instances, substantially all of the actual fragment sequencing signals may be matched to trusted fragment sequencing signals. In some instances, all of the actual fragment sequencing signals may be matched to trusted fragment sequencing signals. In some instances, any percentage, such as at least 10%, 20%, 30%, 40%, 50%, 60%, 70%, 80%, 90%, 95%, 96%, 97%, 98%, 99% or more of the set of actual fragment sequencing signals may be matched to trusted fragment sequencing signals.

In some embodiments, the pairs, or array or pairs, of actual fragment sequencing signals and the best matching trusted fragment sequencing signals in the E. coli key (for the actual fragment sequencing signals) may form a first training set.

Next, the method 100 may comprise using the first training set that includes pairs of {actual fragment sequencing signals of E. coli, and trusted fragment sequencing signals of E. coli} to train a neural network to perform a first mapping (e.g., classification or regression) between actual fragment sequencing signals of E. coli and trusted fragment sequencing signals of E. coli (as in operation 136).

Figure 2:
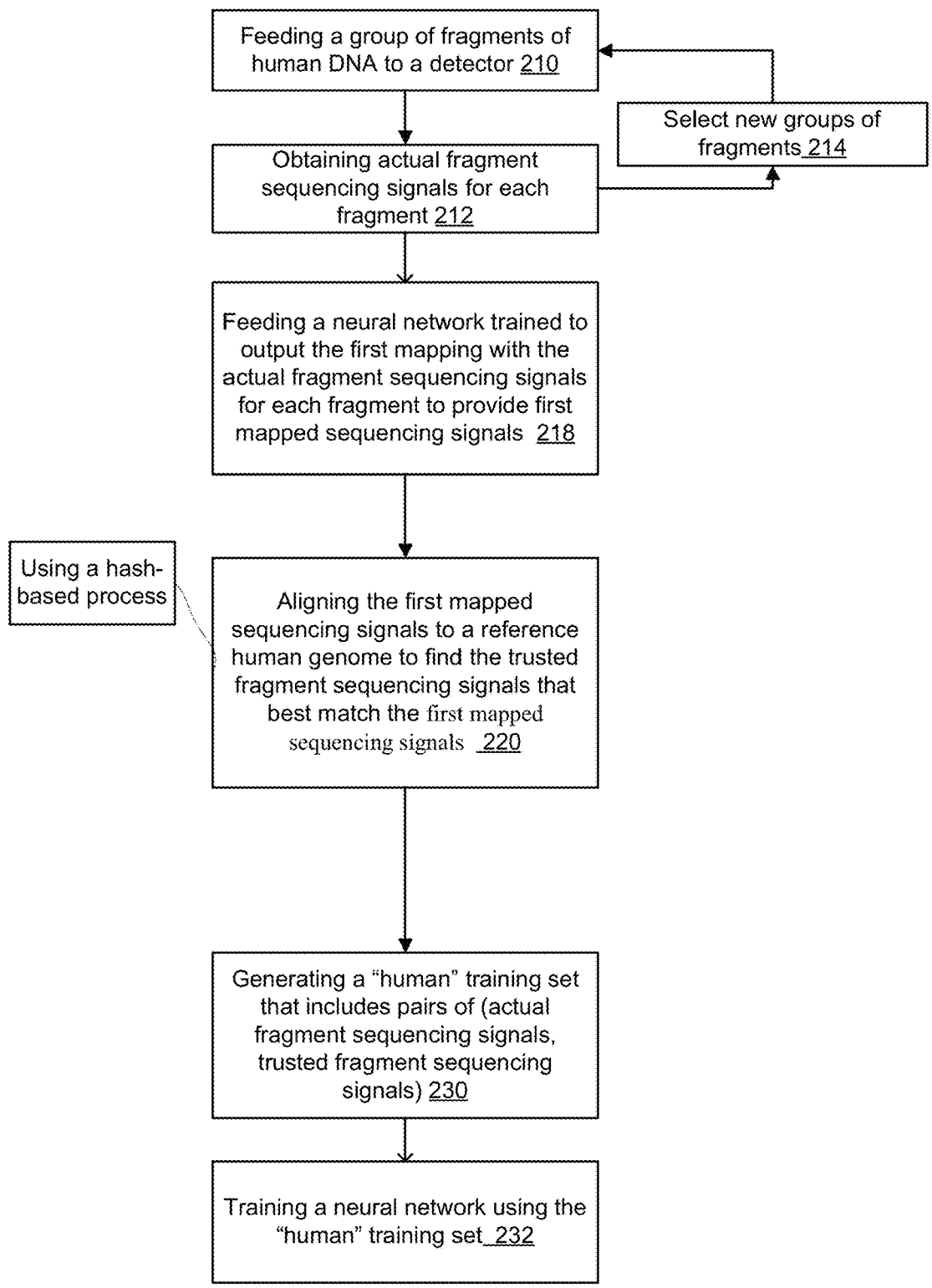
FIG. 2 shows an example of a method 200 for using a neural network (trained to apply the first mapping) for generating a second training set that may be used to map actual fragment sequencing signals of a certain person to trusted fragment sequencing signals of a reference human genome.

FIG. 2 shows an example of a method 200 for using a neural network (trained to apply the first mapping) for generating a second training set that may be used to map actual fragment sequencing signals of a certain person to trusted fragment sequencing signals of a reference human genome.

The method 200 may comprise processing a group of fragments of a human DNA using a detector (as in operation 210). For example, the operation 210 may comprise using a known human DNA of known variants and either ignoring the variants or compensating for the variants.

Next, the method 200 may comprise obtaining actual fragment sequencing signals for each segment (as in operation 212). These actual fragment sequencing signals may be the outputs of the detector.

Next, the method 200 may comprise selecting a new group of fragments (as in operation 214) and proceeding to operation 210. The set of operations 210, 212, and 214 may be repeated or iterated until receiving actual fragment sequencing signals for the entire human genome, or until a substantial amount of actual fragment sequencing signals are received.

In some embodiments, operation 212 may comprise (or may be followed by) rejecting actual fragment sequencing signals that may be defective. For example, while noise-free fragment sequencing signals may be expected to represent an integer number of homopolymers, the actual fragment sequencing signals may provide a non-integer number of homopolymers. The deviation from the expected integer numbers of homopolymers may be indicative of an error in the actual fragment sequencing signals, and once the error exceeds a predefined threshold, the actual fragment sequencing signals may be ignored and may not be processed in operations 218 and 220. The error may be calculated in various manners, for example, mean squared error, and the like. The predefined threshold may be set in any manner.

Next, the method 200 may comprise using a neural network trained to output the first mapping to process the actual fragment sequencing signals for each fragment to provide first mapped sequencing signals (as in operation 218).

Next, the method 200 may comprise aligning the first mapped sequencing signals to a reference human genome to determine the trusted fragment sequencing signals that best match the first mapped sequencing signals (as in operation 220). These trusted fragment sequencing signals may be regarded as best matching the actual fragment sequencing signals. The method 200 may comprise repeating operations 218 and 220 for each of the actual fragment sequencing signals provided in operation 212. In some instances, substantially all of the first mapped sequencing signals may be matched to trusted fragment sequencing signals. In some instances, all of the first mapped fragment sequencing signals may be matched to trusted fragment sequencing signals. In some instances, any percentage, such as at least 10%, 20%, 30%, 40%, 50%, 60%, 70%, 80%, 90%, 95%, 96%, 97%, 98%, 99% or more of the set of first mapped fragment sequencing signals may be matched to trusted fragment sequencing signals.

Next, the method 200 may comprise generating a "human" training set that includes pairs of {actual fragment sequencing signals, and trusted fragment sequencing signals} that correspond to the human genome (as in operation 230).

Next, the method 200 may comprise training a neural network using the "human" training set (as in operation 232). After the training, the neural network is configured apply a second mapping (e.g., classification or regression) between actual fragment sequencing signals corresponding to the human genome and trusted fragment sequencing signals corresponding to the human genome.

Using systems, methods, and media of the present disclosure, a more robust method may be provided when using truncated actual human sequencing signals and truncated trusted reference sequencing signals. Truncating these signals, such as to single-bit actual human sequencing signals and single-bit trusted reference sequencing, may provide a method that is robust to measurement error, while incurring a tolerable cost of finding more candidates for each hash value during the alignment procedure.

After the completion of methods 100 and 200, an estimate of a genome of a subject may be generated.

Figure 3:
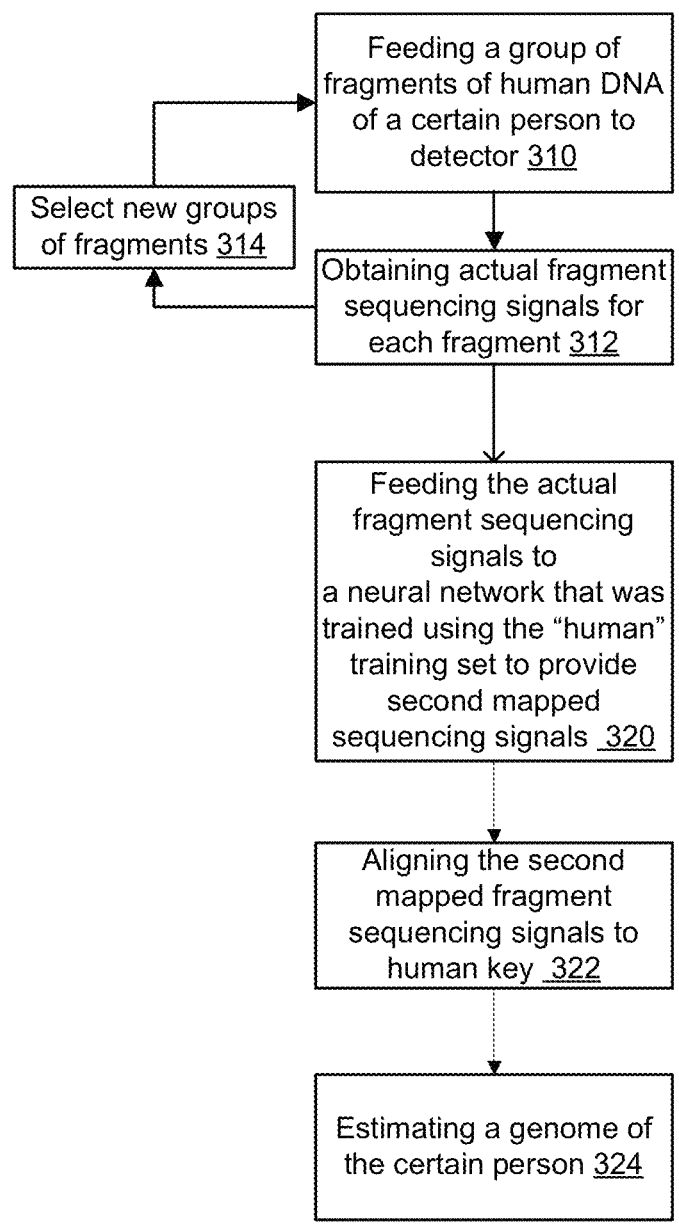
FIG. 3 shows an example of a method 300 for estimating a genome of a certain person.

FIG. 3 shows an example of a method 300 for estimating a genome of a subject.

The method 300 may comprise processing a group of fragments of a human DNA of the subject using the detector.

Next, the method 300 may comprise obtaining actual fragment sequencing signals for each segment (as in operation 312).

In some embodiments, operation 312 may comprise (or may be followed by) assigning a confidence level to actual fragment sequencing signals. For example, while noise-free fragment sequencing signals may be expected to represent an integer number of homopolymers, the actual fragment sequencing signals may provide a non-integer number of homopolymer. The deviation from the expected integer numbers of homopolymers may be indicative of an error in the actual fragment sequencing signals, that may affect the confidence level assigned to the actual fragment sequencing signals.

Next, the method 300 may comprise selecting new group of fragments (as in operation 314) and proceeding to operation 310. The set of operations 310, 312, and 314 may be repeated or iterated until receiving actual fragment sequencing signals for the entire genome of the subject, or until a substantial amount of actual fragment sequencing signals are received.

The method 300 may comprise repeating operations 320 and 322 for each of the actual fragment sequencing signals provided in operation 312.

In some embodiments, operation 320 may comprise processing the actual fragment sequencing signals using a neural network that is trained using the "human" training set to provide second mapped sequencing signals.

Next, the method 300 may comprise aligning the second mapped fragment sequencing signals to a human key (as in operation 322). For example, the alignment may be hash-based.

Next, one or more iterations of operation 322 may be followed by providing an estimate of the genome of the subject (as in operation 324).

Figure 4:
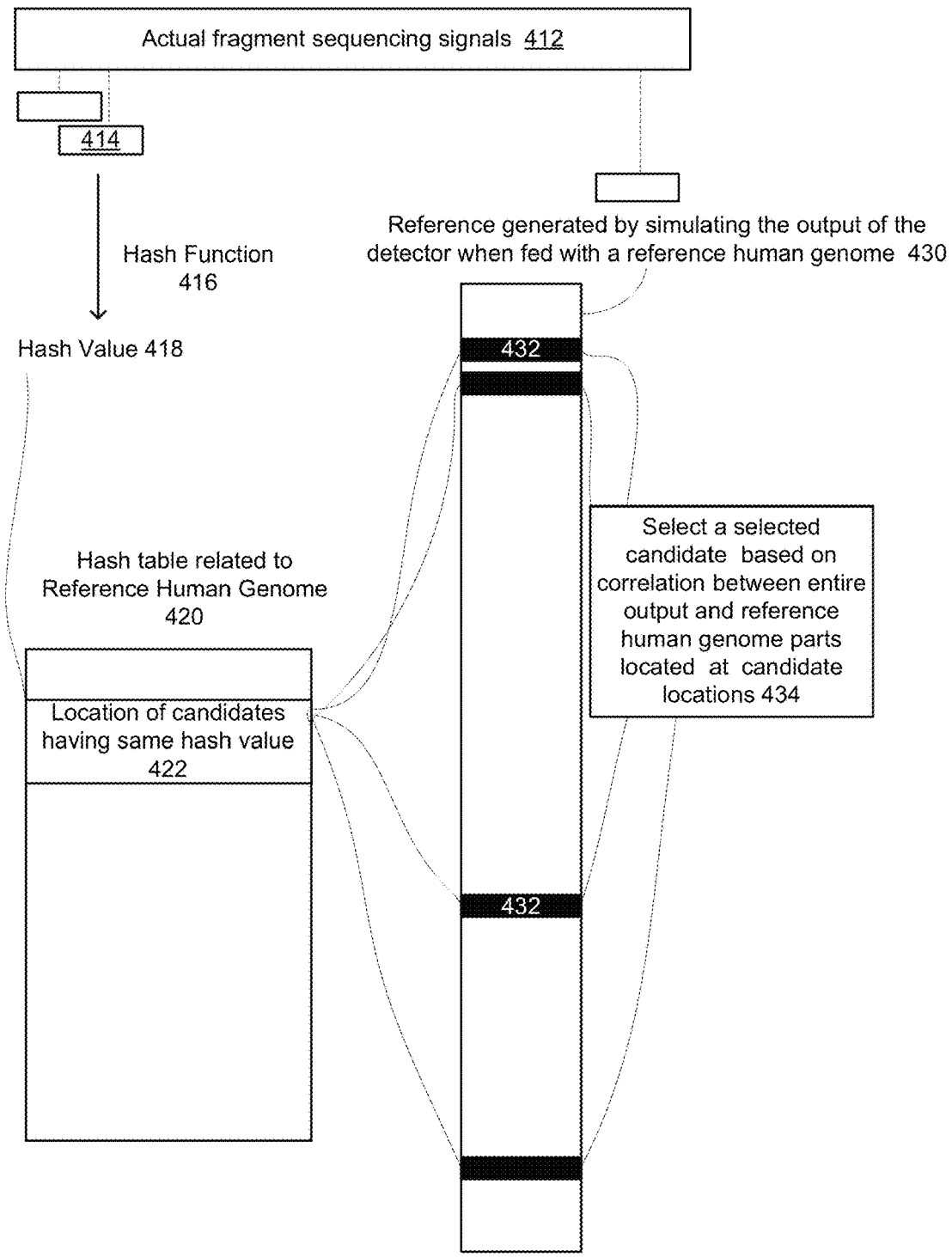
FIG. 4 shows an example of a method for hash-based alignment (e.g., according to operation 322)

FIG. 4 shows an example of a method 400 for hash-based alignment (e.g., according to operation 322).

The method 400 may comprise partitioning actual fragment sequencing signals 412 into smaller partially overlapping portions 414, in order to simplify the execution of operation 322. For example, actual fragment sequencing signals 412 of about one hundred values may be partitioned to portions of about twenty values each.

Next, the method 400 may comprise applying a hash function (416) on each portion to provide a hash value 418.

In some embodiments, the hash value 418 is used as an index to a hash table corresponding to a reference human genome 420.

An entry of the hash table 420 that is accessed by a certain hash value may store the locations of candidates (that have the same hash value) in a data structure, which stores a reference database (430) generated by simulating the output of the detector upon processing a reference human genome. The simulation may assume a substantially error-free process.

Next, the method 400 may comprise using hash value 418 to access entry 422, which stores locations of candidates (432) in the reference database 430.

In some embodiments, the different references are associated with different locations in the reference human genome. In order to select the selected candidate, a correlation (434) between the actual fragment sequencing signals (412) and portions of the reference (430) located at each of the different locations is determined. The selection may include selecting the location with the highest correlation.

Figure 5:
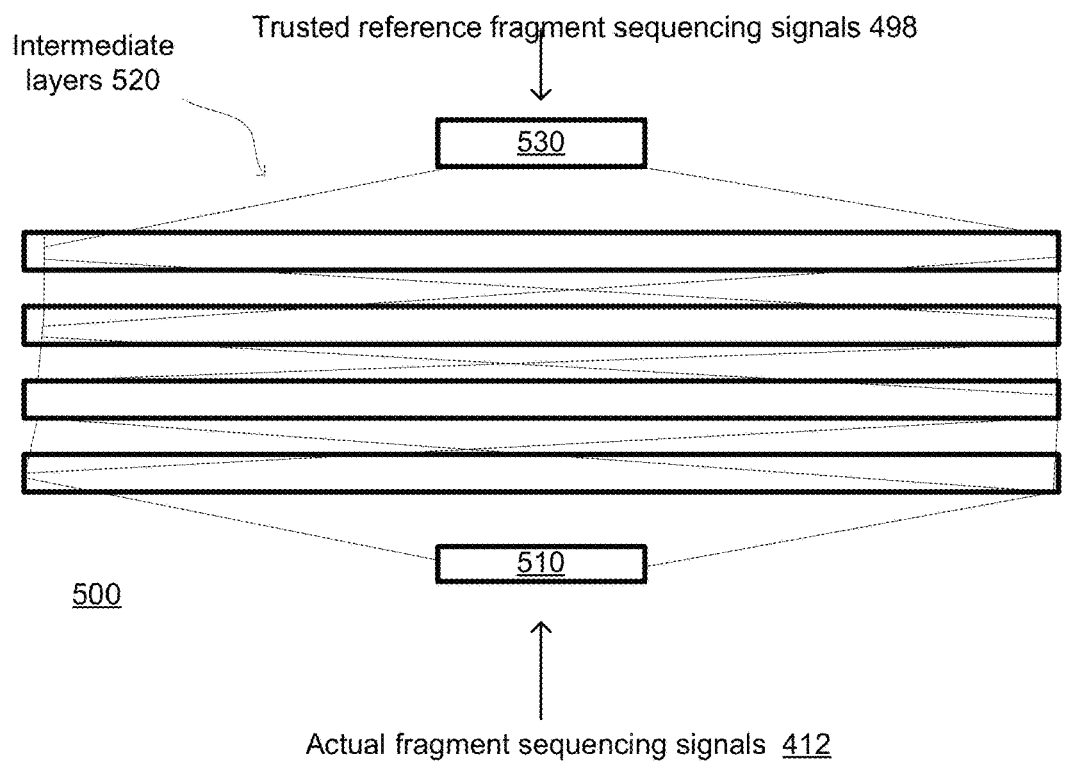
FIG. 5 shows an example of a neural network 500 that may be trained during method 100 and/or method 200—and that may be used during method 300.

FIG. 5 shows an example of a neural network 500 that may be trained during method 100 and/or method 200, which may be used in performing method 300.

The neural network may include an input layer 510, multiple intermediate layers 520, and an output layer 530.

In some embodiments, neural network 500 is a regression network such as a fully connected regression network.

The input layer may include one neuron per actual fragment sequencing signal. For example, if the input layer is fed by actual fragment sequencing signals of one hundred values, then the input layer 510 may include one hundred neurons. A similar example may apply to the output layer. Each intermediate layer may be much larger than the input layer. For example, an intermediate layer may be about 1.5×, 2×, 3×, 4×, 5×, 6×, 7×, 8×, 9×, 10×, or more than 10× larger than the input layer. Other ratios may be used.

Figure 6:
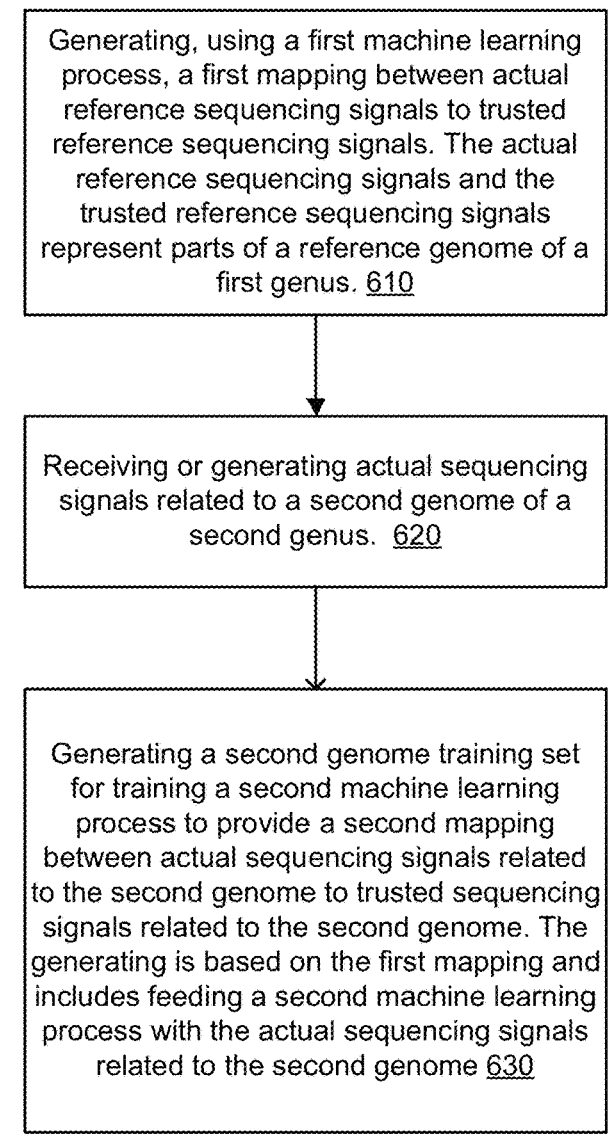
FIG. 6 shows an example of a method 600 for generating a training set.

FIG. 6 shows an example of a method 600 for generating a training set.

The method 600 may comprise generating, using a first trained algorithm (e.g., a machine learning process), a first mapping (e.g., classification or regression) between actual reference sequencing signals to trusted reference sequencing signals. The actual reference sequencing signals and the trusted reference sequencing signals may represent parts of a reference genome of a first genus (e.g., a human genome).

Next, the method 600 may comprise applying the operations of method 100 on a first genome (e.g., a human genome) of a first genus that may differ from *E. coli*.

Next, the method 600 may comprise receiving or generating actual sequencing signals corresponding to a second genome of a second genus (as in operation 620). The first genus may differ from the second genus. The first genome may be smaller than the second genome, for example, by a factor of at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, or 10000. Other factors may be applied.

Next, the method 600 may comprise generating a second genome training set for training a second trained algorithm (e.g., machine learning process) to provide a second mapping (e.g., classification or regression) between actual sequencing signals corresponding to the second genome to trusted sequencing signals corresponding to the second genome (as in operation 630).

Operation 630 may be performed based on the first mapping, and may include using a second trained algorithm (e.g., machine learning process) to process the actual sequencing signals corresponding to the second genome.

Operation 630 may apply the operations of method 200 on a second genome of a second genus that may differ from human (e.g., *E. coli*).

Operation 630 may be followed by training a trained algorithm (e.g., machine learning process) using the second genome training set.

In some embodiments, the first trained algorithm (e.g., machine learning process) may differ from the second trained algorithm (e.g., machine learning process) or may be the same as the second trained algorithm (e.g., machine learning process).

Figure 7:
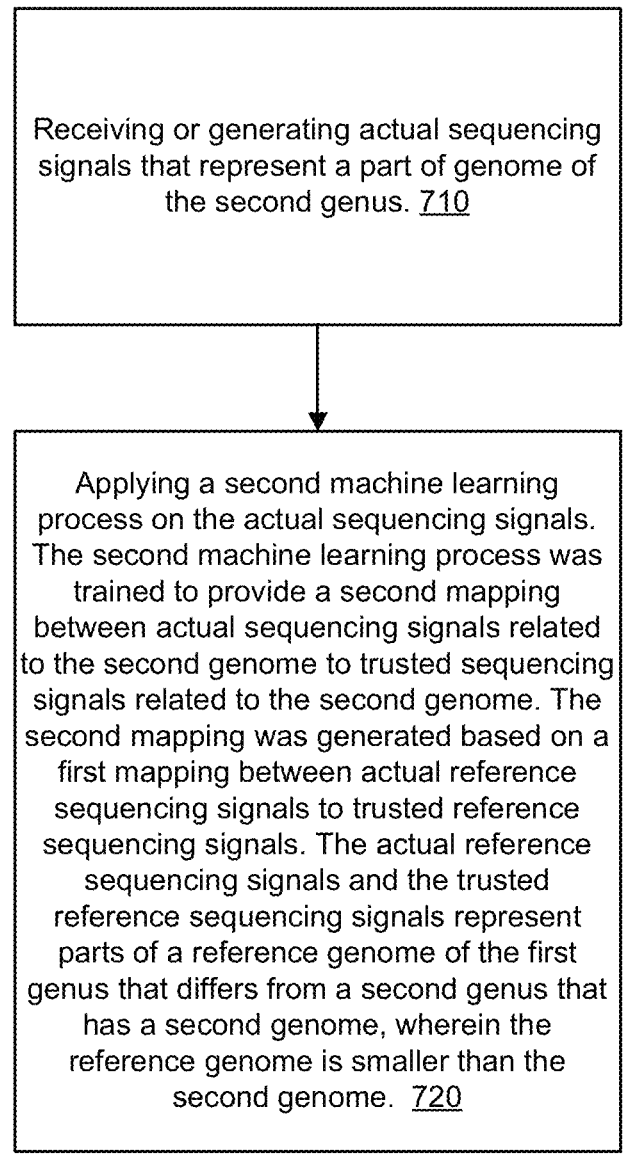
FIG. 7 shows an example of a method 700 for estimating a genome of a certain entity of a second genus. The estimation is based on a first genus and method 700 may be referred to as a method for first genus-based estimation of a genome of a second genus.

FIG. 7 shows an example of a method 700 for estimating a genome of a certain entity (e.g., a subject) of a second genus. The estimation may be performed based on a first genus, and method 700 may be referred to as a method for first genus-based estimation of a genome of a second genus.

The method 700 may include performing operations 710 and 720 for each part of the genome of the certain entity (e.g., a subject) of the second genus, out of multiple parts of the genome of the second genus. The method 700 may comprise performing one or more repetitions or iterations of the set of operations 710 and 720 to provide the estimate of the genome of the certain entity (e.g., a subject) of the second genus.

The operation 710 may comprise receiving or generating actual sequencing signals that represent a part of genome of the second genus.

The operation 720 may include estimating the part of the genome of the certain entity (e.g., a subject) of the second genus.

The operation 720 may comprise applying a second trained algorithm (e.g., machine learning process) to the actual sequencing signals. The second trained algorithm (e.g., machine learning process) may be trained to provide a second mapping (e.g., classification or regression) between actual sequencing signals corresponding to the second genome and trusted sequencing signals corresponding to the second genome. The second mapping may be generated based on a first mapping between actual reference sequencing signals and trusted reference sequencing signals. The actual reference sequencing signals and the trusted reference sequencing signals may represent parts of a reference genome of the first genus that differ from a second genome of a second genus. The reference genome may be smaller than the second genome.

Operations 710 and 720 may comprise applying the operations of method 300 on a second genus that may differ from human, wherein the first mapping may relate to a first genus other than *E. coli*.

Trained Algorithms

After processing biological samples to generate sequencing signals of nucleic acids, a trained algorithm may be used to process the sequencing signals to perform sequencing calling (e.g., determining the base calls based on the sequence signals). For example, the trained algorithm may be used to determine quantitative measures of sequence signals at each of a plurality of nucleotide positions of the nucleic acids. The trained algorithm may be configured to determine the quantitative measures of the sequence signals an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99%.

The trained algorithm may comprise a supervised machine learning algorithm. The trained algorithm may comprise a classification and regression tree (CART) algorithm. The supervised machine learning algorithm may comprise, for example, a Random Forest, a support vector machine (SVM), a neural network, or a deep learning algorithm. The trained algorithm may comprise an unsupervised machine learning algorithm.

The trained algorithm may be configured to accept a plurality of input variables and to produce one or more output values based on the plurality of input variables. The plurality of input variables may be generated based on processing sequencing signals of nucleic acids. For example, an input variable may comprise a number of sequences corresponding to or aligning to a reference genome or genomic loci of a reference genome. As another example, an input variable may comprise analog values of sequencing signals produced by a sequencer.

The trained algorithm may comprise a classifier, such that each of the one or more output values comprises one of a fixed number of possible values (e.g., a linear classifier, a logistic regression classifier, etc.) indicating a classification of the sequencing signals by the classifier. The trained algorithm may comprise a binary classifier, such that each of the one or more output values comprises one of two values (e.g., {0, 1}, {positive, negative}, or {present, absent}) indicating a classification of the sequencing signals by the classifier. The trained algorithm may be another type of classifier, such that each of the one or more output values comprises one of more than two values (e.g., {0, 1, 2}, {positive, negative, or indeterminate}, {present, absent, or indeterminate}, {A, C, G, T}, or {A, C, G, U}) indicating a classification of the sequencing signals by the classifier. The output values may comprise descriptive labels, numerical values, or a combination thereof. Some of the output values may comprise descriptive labels. Such descriptive labels may provide an identification of base calls of the sequence signals, and may comprise, for example, {A, C, G, T}, or {A, C, G, U}. Such descriptive labels may provide an indication of context for a base call, or a confidence or accuracy for a base call. As another example, such descriptive labels may provide a relative assessment of the likelihood of different bases being called for the sequencing signals. Some descriptive labels may be mapped to numerical values, for example, by mapping "positive" or "present" to 1, and "negative" or "absent" to 0.

Some of the output values may comprise numerical values, such as binary, integer, or continuous values. Such binary output values may comprise, for example, {0, 1}, {positive, negative}, or {present, absent}. Such integer output values may comprise, for example, {0, 1, 2}. Such continuous output values may comprise, for example, a probability value of at least 0 and no more than 1 (e.g., indicative of the likelihood of a base call for a sequencing signal). Such continuous output values may comprise, for example, an un-normalized probability value of at least 0. Some numerical values may be mapped to descriptive labels, for example, by mapping 1 to "positive" or "present", and 0 to "negative" or "absent".

Some of the output values may be assigned based on one or more cutoff values. For example, a binary classification of sequencing signals may assign an output value of "positive" or 1 if the sequencing signal at a particular nucleotide position has at least a 50% probability of being called as a given base (e.g., A, C, G, T, or U). For example, a binary classification of samples may assign an output value of "negative" or 0 if the sequencing signal at a particular nucleotide position has at least a 50% probability of being called as a given base (e.g., A, C, G, T, or U). In this case, a single cutoff value of 50% is used to classify bases of sequencing signals into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of sequencing signals may assign an output value of "positive" or 1 if the sequencing signal at a particular nucleotide position has a probability of being called as a given base (e.g., A, C, G, T, or U) of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of sequencing signals may assign an output value of "positive" or 1 if the sequencing signal at a particular nucleotide position has a probability of being called as a given base (e.g., A, C, G, T, or U) of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of sequencing signals may assign an output value of "negative" or 0 if the sequencing signal at a particular nucleotide position has a probability of being called as a given base (e.g., A, C, G, T, or U) of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of sequencing signals may assign an output value of "negative" or 0 if the sequencing signal at a particular nucleotide position has a probability of being called as a given base (e.g., A, C, G, T, or U) of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classification of sequencing signals may assign an output value of "indeterminate" or 2 if the sample is not classified as "positive", "negative", 1, or 0. In this case, a set of two cutoff values is used to classify sequencing signals into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify sequencing signals into one of n+1 possible output values, where n is any positive integer.

The trained algorithm may be trained with a plurality of independent training samples. Each of the independent training samples may comprise sets of sequencing signals generated from nucleic acids (e.g., from biological sample of a subject) and one or more known output values corresponding to the sequencing signals (e.g., a set of base calls or a nucleotide sequence corresponding to the sequencing signals). Independent training samples may be obtained or derived from a plurality of different subjects. Independent training samples may comprise sets of sequencing signals generated from nucleic acids (e.g., from biological sample of a subject) and one or more known output values corresponding to the sequencing signals (e.g., a set of base calls or a nucleotide sequence corresponding to the sequencing signals) obtained at a plurality of different time points from the same subject (e.g., on a regular basis such as weekly, biweekly, or monthly).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The trained algorithm may be trained with no more than about 500, no more than about 450, no more than about 400, no more than about 350, no more than about 300, no more than about 250, no more than about 200, no more than about 150, no more than about 100, or no more than about 50 independent training samples.

The trained algorithm may be configured to identify base calls of the sequencing signals at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The accuracy of identifying the base calls of the sequencing signals by the trained algorithm may be calculated as the percentage of base calls that are correctly identified or classified (e.g., presence or absence of a particular base).

The trained algorithm may be configured to identify base calls of the sequencing signals with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the base calls of the sequencing signals using the trained algorithm may be calculated as the percentage of base calls identified or classified as being present that correspond to bases that are truly present.

The trained algorithm may be configured to identify base calls of the sequencing signals with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the base calls of the sequencing signals using the trained algorithm may be calculated as the percentage of base calls identified or classified as being absent that correspond to bases that are truly absent (e.g., not present).

The trained algorithm may be adjusted or tuned to improve one or more of the performance, accuracy, PPV, or NPV of identifying the base calls of the sequencing signals. The trained algorithm may be adjusted or tuned by adjusting parameters of the trained algorithm (e.g., a set of cutoff values used to identify base calls of sequencing signals, as described elsewhere herein, or weights of a neural network). The trained algorithm may be adjusted or tuned continuously during the training process or after the training process has completed.

After the trained algorithm is initially trained, a subset of the inputs may be identified as most influential or most important to be included for making high-quality classifications. The plurality of input variables or a subset thereof may be ranked based on classification metrics indicative of each input variable's importance toward making high-quality classifications or identifications of base calls of sequencing signals. Such metrics may be used to reduce, in some cases significantly, the number of input variables (e.g., predictor variables) that may be used to train the trained algorithm to a desired performance level (e.g., based on a desired minimum accuracy, PPV, or NPV, or a combination thereof). For example, if training the trained algorithm with a plurality comprising several dozen or hundreds of input variables in the trained algorithm results in an accuracy of classification of more than 99%, then training the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics.

The present disclosure provides computer systems that are programmed to implement methods of the disclosure. In some embodiments, a neural network used to implement method 100 and/or method 200 may be a U-Net.

U-Net is a convolutional neural network that was developed for biomedical image segmentation at the Computer Science Department of the University of Freiburg, Germany. The network may be based on the fully convolutional neural network, and its architecture is modified and extended to work with fewer training images and to yield more precise segmentations. For example, segmentation of a 512×512 image may be performed using a U-Net in less than a second on a modern GPU.

The U-net may be a combination of two deep learning methods: a convolutional neural network (CNN) and an Encoder-Decoder. The CNN may be configured to handle large input images with a relatively small number of weights in the network. This is possible because the input image is typically position invariant—the filter operated in one section of the input image is the same as those in other sections of the input image. Therefore, the CNN applies the same filters in all parts of the input image, thereby allowing optimization with a reasonable number of parameters, and achieving the machine learning process to be performed with a manageable number of samples in a reasonable time. The encoder-decoder is a method for performing dimensionality reduction in a machine learning process. It may comprise having a network map all the input variables to a small number of weights, and decoding the weights back to the input image. This technique enables using information from the entire input image with a small number of parameters.

The U-Net may use both the CNN and encoder-decoder techniques in parallel, thereby allowing for repeated reuse of the same filter in the input image and considering large scale effect of the image.

Methods, systems, and media of the present disclosure may perform the processing of actual human fragment sequencing signals in a similar manner as that used for Semantic Segmentation, by leveraging some parallel elements.

In some embodiments, actual human fragment sequencing signals may be treated as a single dimension (1D) image. Both input images and actual human fragment sequencing signals may exhibit the property of having most of the information be flow invariant—as the sequence calling or base calling of the actual human fragment sequencing signals may comprise analysis of the values of the actual human fragment sequencing signals and on the immediate surrounding values of the actual human fragment sequencing signals. Nevertheless, the processing of the actual human fragment sequencing signals may also use information from the entire read, therefore using the encoder part of the network may be beneficial.

The U-Net may be fed by various types of information. The different types of information can be seen as different information channels. For example, the different information types may include the actual human fragment sequencing signals and may also include one or more other additional types of information. As an example, an additional type of information may include calculation of the photometry background noise, which was found to be beneficial information.

As another example, an additional type of information may include the sequencing signals obtained from the preamble. The preamble may be attached to the tested human genome fragments, and may be known in advance. The sequencing signals obtained from the preamble may be expected to be substantially the same for all reads. The intensity of the sequencing signals obtained from the preamble may be indicative of an approximation of the number of strands in the bead. It can be useful in a normalization of the sequencing signals obtained from the preamble.

As another example, an additional type of information may include local information corresponding to the vicinity of the readings. For example, the local information may represent readings with a tile, such as a reading per flow. A substrate that supports the samples may be virtually segmented to tiles (for example, tents till thousands of tiles), and the local information may reflect readings corresponding to a given tile. For example, the readings may be calculated as a mean signal for all beads in the photometry image tile and per flow. Other functions (such as weighted sums, linear or non-linear functions may be used). This local information may be used for compensating for non-uniformity across the substrate (for example, some tiles may be illuminated with stronger radiation than another tile).

As another example, an additional type of information may include information indicative of the flow base (base used during the flow) and/or the flow position. Such additional information may include a flow base synthetic integer vector and a flow position synthetic integer vector. Any other representation of the fourth additional type of information may be provided.

A U-net of systems, methods, and media of the present disclosure can be, for example, a 6-layer CNN model parallel concatenated to an encoder-decoder. The model may include a number of parameters of about 1 thousand, 5 thousand, 10 thousand, 50 thousand, 100 thousand, 200 thousand, 300 thousand, 400 thousand, 500 thousand, 600 thousand, 700 thousand, 800 thousand, 900 thousand, 1 million, or more than 1 million. Further, the model may be trained using about 1 million, 5 million, 10 million, 15 million, 20 million, 25 million, 30 million, 35 million, 40 million, 45 million, 50 million, 55 million, 60 million, 65 million, 70 million, 75 million, 80 million, 85 million, 90 million, 95 million, 100 million, 150 million, 200 million, 250 million, 300 million, 350 million, 400 million, 450 million, 500 million, 600 million, 700 million, 800 million, 900 million, or 1 billion reads. Reads representing the ground truth may be created by alignment, and reads used in the training may be selected based on a high confidence of alignment. Reads with suspected variance and reads where the information ends before the end of the sequence may be discarded from training.

Figure 8:
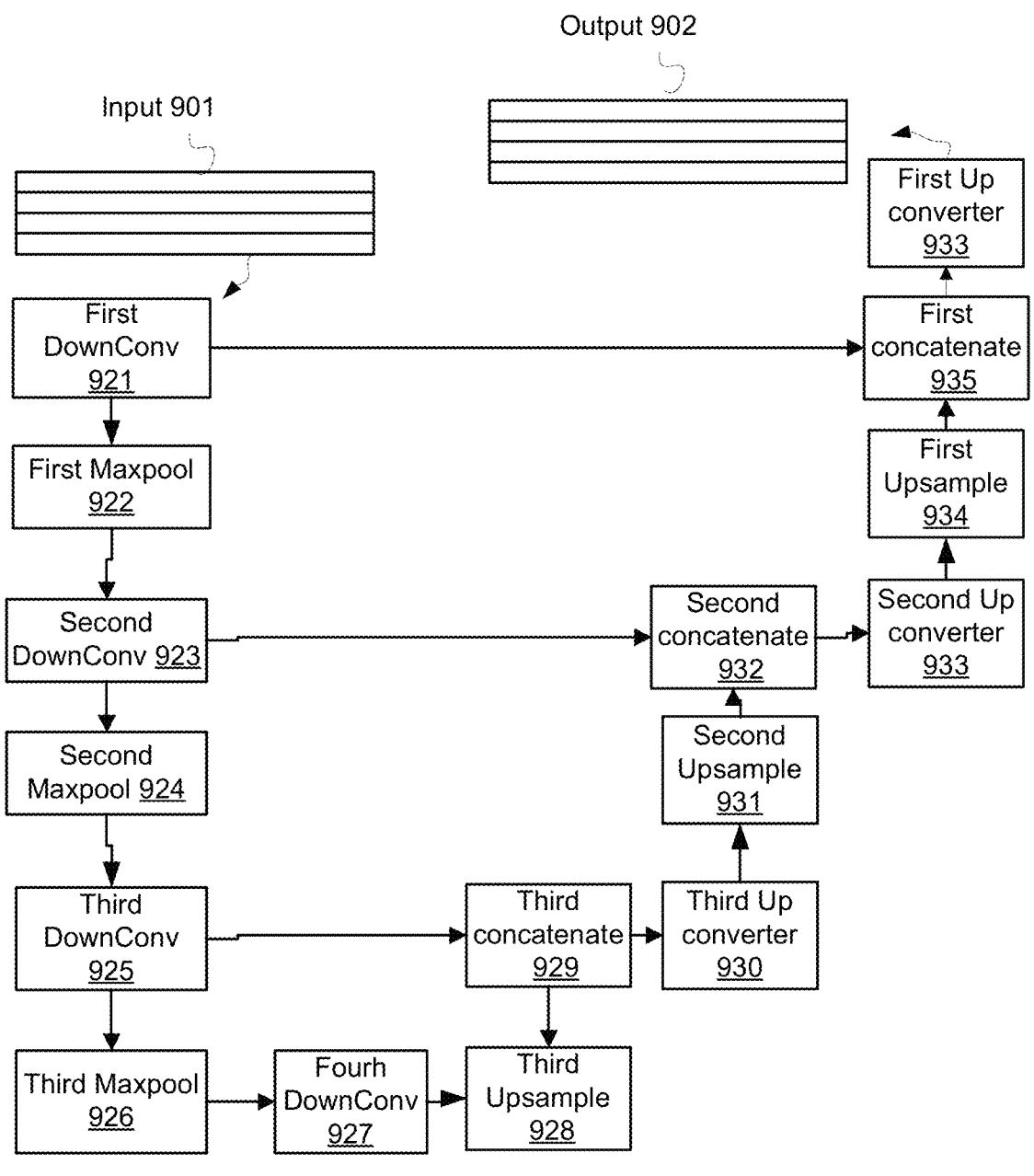
FIG. 8 shows an example of a U-Net type neural network that is trained to estimate a genome of a certain entity of a second genus.

FIG. 8 shows an example of a U-Net 900 that is trained to estimate a genome of a certain entity of a second genus. The U-net 900 may be trained and/or used according to one or more operations of method 100 and/or 200. The U-net may be fed with input 901, which may include actual human fragment sequencing signals and optionally one or more other additional types of information, and an output 902 that may include, for example, accurate human fragment sequencing signals.

U-Net 900 includes first till fourth down-convolution units ("DownConv") 921, 923, 92, 5 and 927, first till third maxpool units 922, 924, and 926, first till third upsample units 934, 931, and 928, first till third concatenate units 935, 932, and 929, and first till third up-convolution units 933, 933, and 930.

Figure 10:
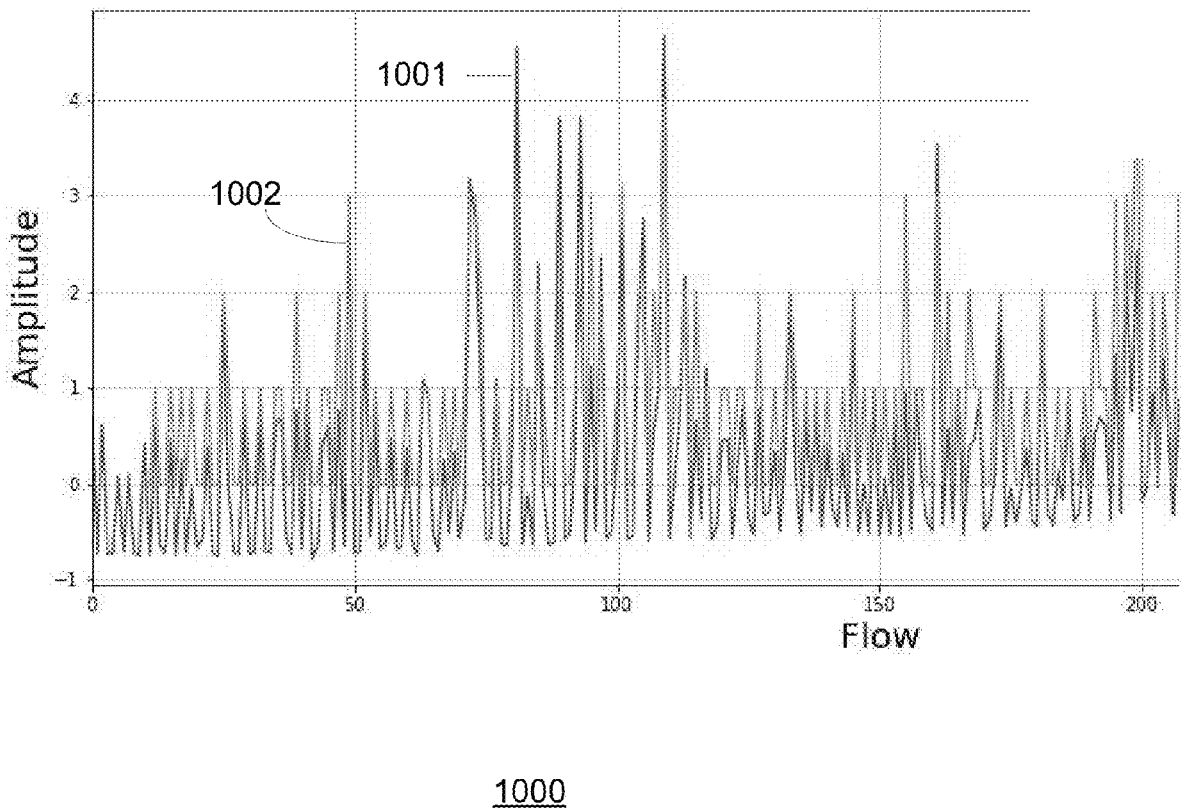
FIG. 10 shows an example of a graph 1000 that illustrates input signals 1001 and output signals 1002 of a neural network trained to estimate a genome of a certain entity of a second genus.
Figure 11:
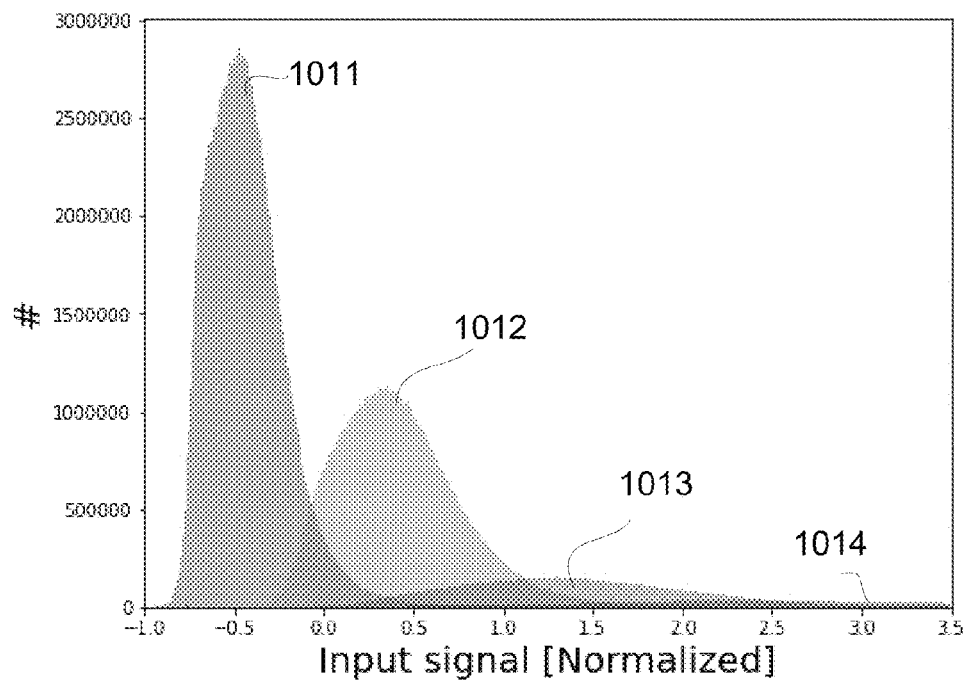
FIG. 11 shows an example of an input signal histogram 1010 and an output signal histogram 1020 of a neural network trained to estimate a genome of a certain entity of a second genus.
Figure 11:
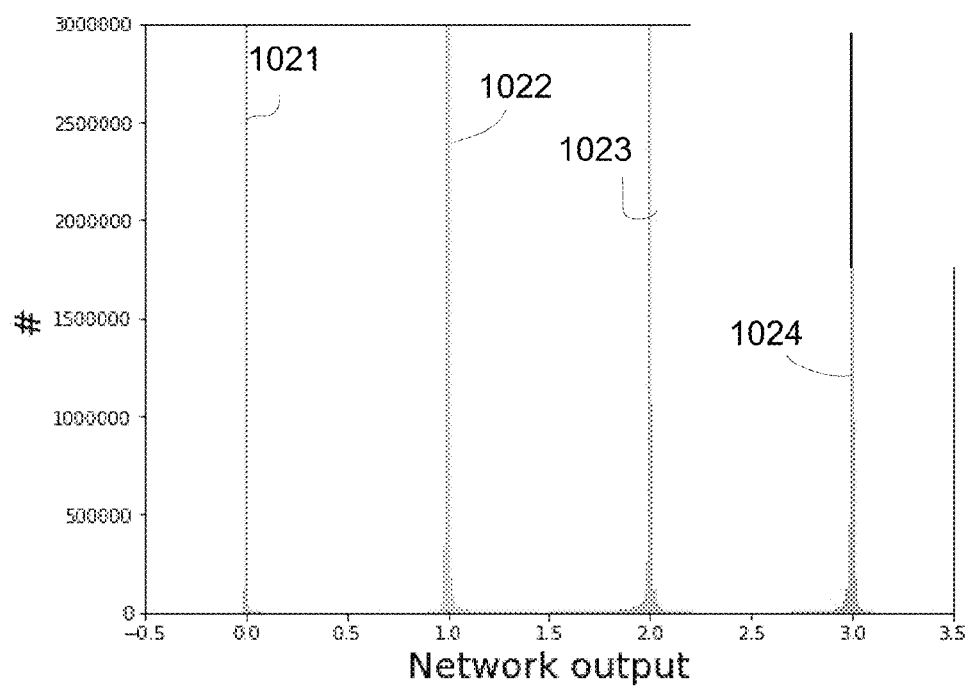

FIGS. 10 and 11 show examples of an input signal that are fed to a neural network and an output generated by the neural network. The input signals comprise actual sequencing signals (e.g., having inaccuracies and noise) that represent a measured number of nucleotides per homopolymer and the output signal comprises noise-free (or noise-reduced) signals that represent the estimated number of nucleotides per homopolymer.

FIG. 10 shows an example of a graph 1000 that illustrates input signals 1001 and output signals 1002. The output signals 1002 converge around 0, 1, 2, and 3 nucleotides per homopolymer, while the input numbers 1001 cover a larger range of values.

FIG. 11 shows an example of an input signal histogram 1010 and an output signal histogram 1020.

A first distribution 1011 of input values are mapped by the neural network to a first narrow distribution 1021 (which may be approximately a delta function) about value zero.

A second distribution 1012 of input values are mapped by the neural network to a second narrow distribution 1022 (which may be approximately a delta function) about value one.

A third distribution 1013 of input values are mapped by the neural network to a third narrow distribution 1023 (which may be approximately a delta function) about value two.

A fourth distribution 1014 of input values are mapped by the neural network to a fourth narrow distribution 1024 (which may be approximately a delta function) about value three.

In some embodiments, a computer system may be used to perform operations of methods of the present disclosure over time and to generate one or more estimates of genomes of one or more organisms.

In some embodiments, at least one of mechanical conditions, inspection conditions, collection conditions, and chemical conditions may change over time, thereby causing one or more models that were once accurate to become inaccurate. Accordingly, the model may be replaced, adjusted, or amended over time as needed. For example, the amendment may include initially using an initial model that was produced at the initial setup of the computer system. Any method as disclosed herein may be used to generate the initial model.

In some embodiments, the initial model is amended and/or replaced over time. For example, the initial model may be amended or replaced by retraining a trained algorithm (e.g., machine learning process) using new actual sequencing signals. The new actual sequencing signals may comprise information acquired during one or more completed estimations or information that was not previously processed.

In some embodiments, the model replacement or change occurs in a periodic manner, in response to certain events, after running each estimation, and/or after running multiple (n) estimations. In other cases, the model replacement or change may be triggered upon manual calibration procedures.

A model replacement may occur based on an evaluation of a current model, such as inferring a sample of new actual sequencing signals using the model that was used in a previous estimation. From the sample, a ground truth may be created using an alignment procedure. The inferred results and the new ground truth may be compared, and an error rate or any other reliability or accuracy score may be calculated. If the result is accurate enough, then the current model may be maintained. If the result is not accurate enough, then the sample data may be used to train a trained algorithm (e.g., machine learning process) to provide a new model for the new actual sequencing signals.

The retraining of a trained algorithm (e.g., machine learning process) may comprise training the machine learning process to generate a new model from the start (e.g., de novo) or obtaining a previously used model and running one or more epochs to update the model.

The retraining may be executed in various manners, such as applying transfer learning and adjusting only a part of the model (for example, adjusting a few initial input layers in the model). Such efficient retraining may be needed as training time constraints may become critical.

Figure 12:
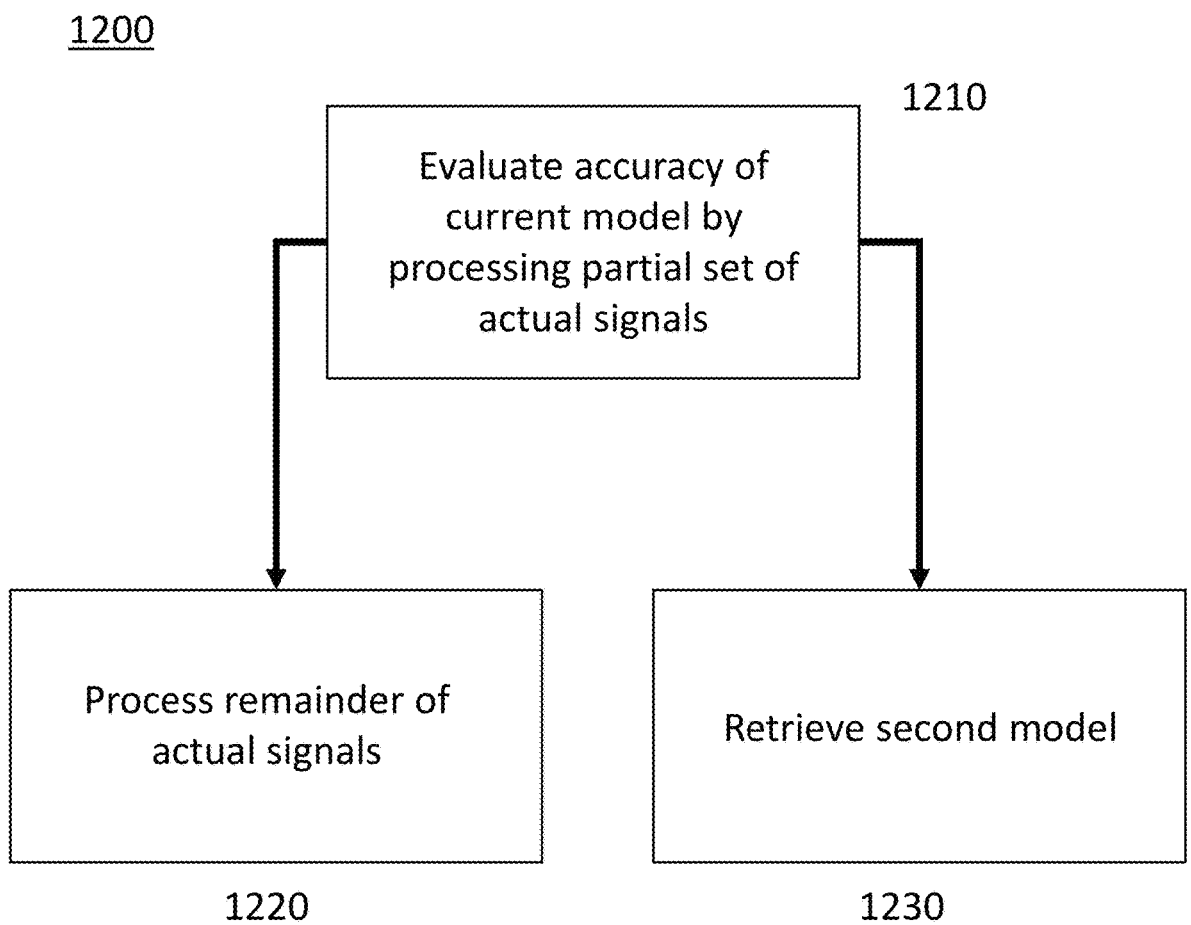
FIG. 12 shows an example of a method for estimating a genome of a genus.

FIG. 12 illustrates an example of a method 1200 for estimating a genome of a genus.

The method 1200 may comprise (a) receiving or generating actual sequencing signals that represent a first part of the genome of the genus; (b) applying a current model on at least a portion of the actual sequencing signals to provide partial current results; wherein the current model is generated by a trained algorithm (e.g., machine learning process); (c) evaluating an accuracy of the partial current results; and (d) determining, based on the accuracy of the partial current results, whether to continue using the current model for completing the estimation of the genome (e.g., using the current genome) (as in operation 1210). The accuracy of the partial current results may be evaluated using any of the methods described herein (e.g., processing against ground truth).

If the method 1200 has determined to continue using the current model, then operation 1210 may be followed by completing the estimation of the genome using the current model (as in operation 1220).

If the method 1200 has determined not to continue using the current model, then operation 1210 may be followed by obtaining a second model having sufficient estimation accuracy, and estimating the genome (e.g., of the second genus) using the second model (as in operation 1230). In some instances, the current model may be retrained or amended and operation 1210 repeated until it is determined that the evaluated model has sufficient accuracy.

In some embodiments, the current model is generated based on information corresponding to a reference genome that is smaller than (e.g., significantly smaller than) the genome of the genus. For example, as described in any of the methods disclosed herein, a first genome (reference genome) may be used that is shorter than the second genome (genome).

The estimation may be executed by a computer system. In some embodiments, at least one model that was used by the computer system prior to using the current model is generated based on information corresponding to a reference genome that is smaller (e.g., significantly smaller) than the genome of the genus. This at least one model may be the initial model or any other model.

In some embodiments, the method 1200 may comprising executing a plurality of iterations of the set of operations 1210, 1220, and 1230.

FIG. 13 illustrates an example of a method 1300 for estimating genomes of a plurality of organisms of a genus.

The method 1300 may comprise performing a plurality of different estimation processes for estimating the genomes of the plurality of organisms (as in operation 1310).

In some embodiments, performing the plurality of estimation processes comprises using a plurality of different estimation models.

In some embodiments, at least one of the plurality of different models is generated by retraining a trained algorithm (e.g., machine learning process) to provide a new and/or amended model (as in operation 1320).

In some embodiments, the retraining is performed based, at least in part, on information corresponding to a reference genome that is smaller (e.g., significantly smaller) than the genome of the genus (e.g., a second genome).

In some embodiments, the at least one of the plurality of different models is generated based on information corresponding to a reference genome that is smaller (e.g., significantly smaller) than the genome of the genus.

In some embodiments, the method 1300 may comprise replacing a model of the plurality of different models by a second model during each of a plurality of predefined durations of time (as in operation 1330).

In some embodiments, the method 1300 may comprise replacing a model of the plurality of different models by a second model during each of a plurality of predefined numbers of estimation processes.

In some embodiments, the method 1300 may comprise replacing a model of the plurality of different models by a second model based on an evaluation of an accuracy of the model.

Figure 14:
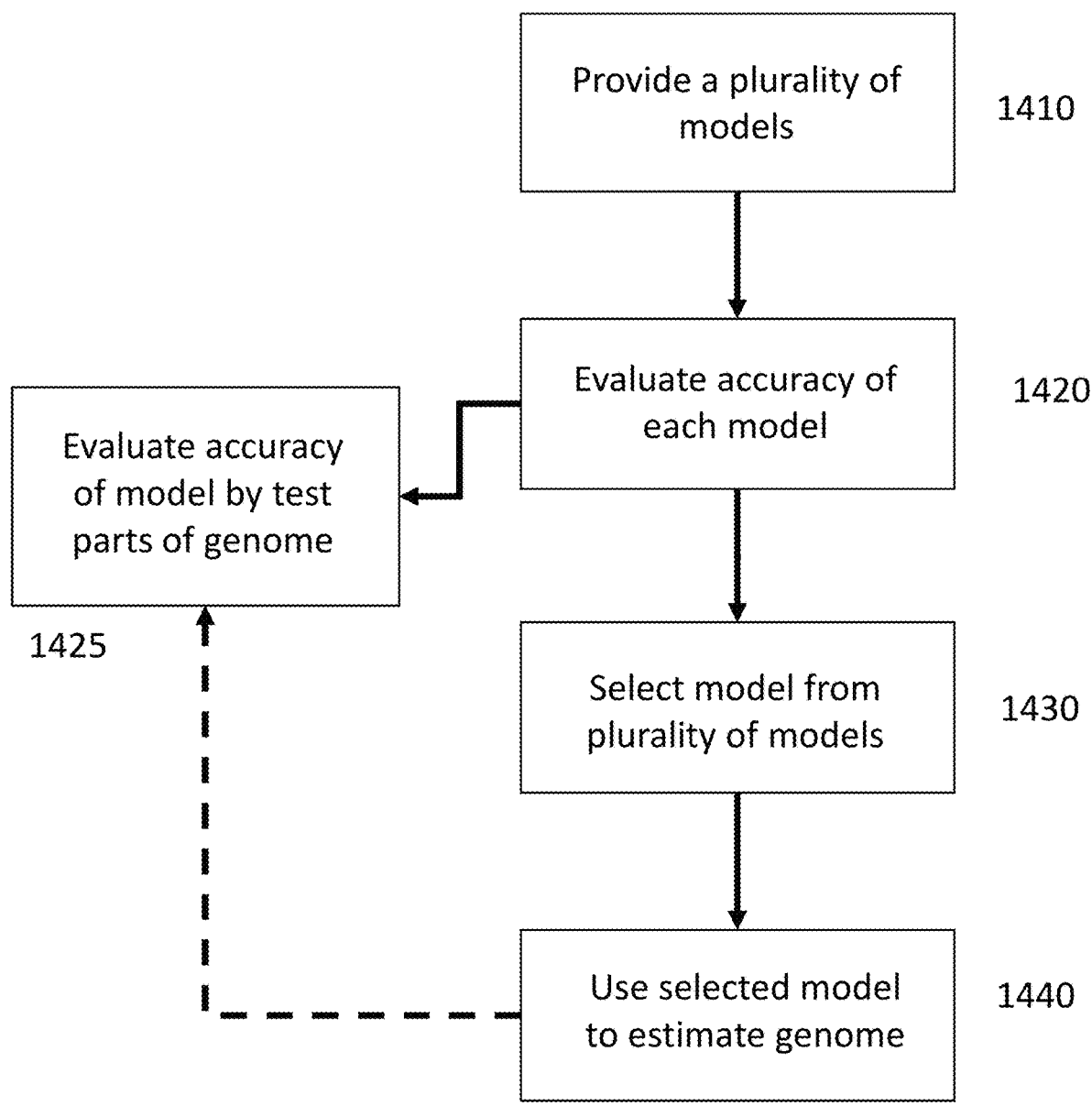
FIG. 14 shows an example of a method for estimating a genome of a genus.

FIG. 14 illustrates an example of a method 1400 for estimating a genome of a genus.

The method 1400 may comprise estimating the genome of the genus. The estimating may include providing a plurality of models (as in operation 1410); selecting a model to be used during the estimation process, out of a plurality of models (as in operation 1430); and using the selected model to estimate the genome (as in operation 1440).

The selecting may be performed based on an estimate regarding an accuracy of the estimation corresponding to the plurality of models (as in operation 1420).

The estimate may be performed based on tests made on parts of the genome (as in operation 1425). The accuracy of the model may be evaluated using any of the methods described herein (e.g., processing against ground truth). For example, the accuracy of the model may be evaluated using a statistical measure of error, such as an R-squared value, a mean squared error (MSE), a root mean squared error (RMSE), a sum of squares error (SSE), a mean absolute error (MAE), a mean absolute percentage error (MAPE), etc. (e.g., where a lower measure of error indicates a higher accuracy of the model). In some instances, each model may be tested on a single portion of the genome, or multiple portions of the genome. In some instances, a model may be evaluated by testing a reference genome. In some instances, a model may be evaluated by testing another genome. For example, one or more portions of the genome may be compared to a reference genome or another genome to evaluate the accuracy of the model.

In alternative embodiments, the method 1400 may comprise selecting one or more models from a plurality of models, and using the selected one or more models to estimate the genome. For example, the same genome may be estimated based on a plurality of model to generate a plurality of estimates. The plurality of estimates may be further processed to, for example, generate a consolidated estimate. The plurality of estimates may be used to evaluate the selected models (as in operation 1425), such as to determine, if one or more of such selected models have to be retrained and/or amended. For example, an estimate that diverges substantially from a remainder of the estimates may be indicative of an inaccurate model.

Provided is a method for estimation of a genome of a genus. The method may comprise performing a plurality of different estimation processes for estimating the genomes of a plurality of multiple organisms; wherein an estimation process of the plurality of different estimation processes comprises selecting a model from among a plurality of different models to be used during the estimation process.

In some embodiments, the selecting is based on an estimate regarding an accuracy of the estimation corresponding to the plurality of models.

In some embodiments, the estimate is based on tests made on parts of the genome.

In some embodiments, the estimating is performed by a computer system.

Figure 15:
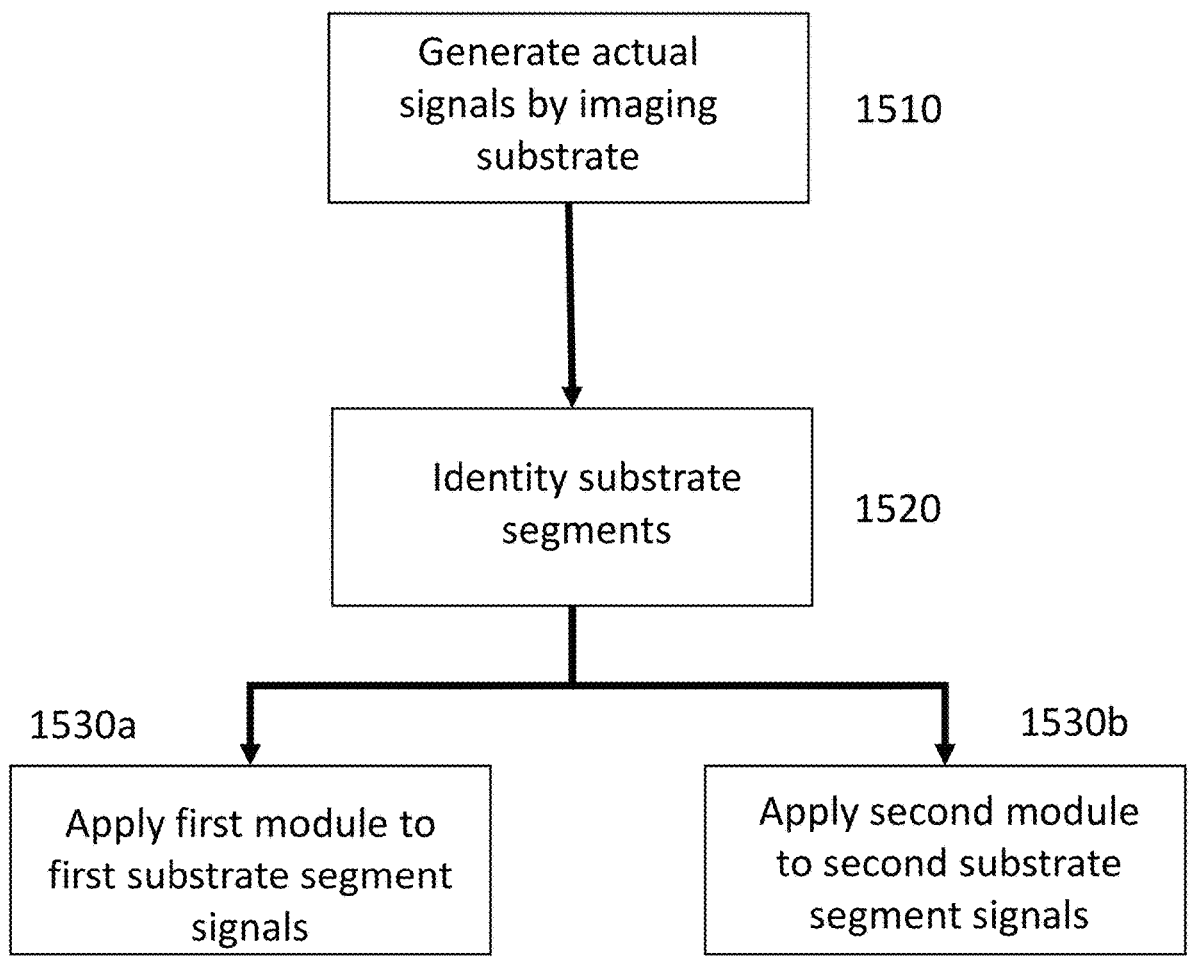
FIG. 15 shows an example of a method for estimating a genome of a genus.

FIG. 15 illustrates an example of a method 1500 for estimating a genome of a genus.

Figure 16:
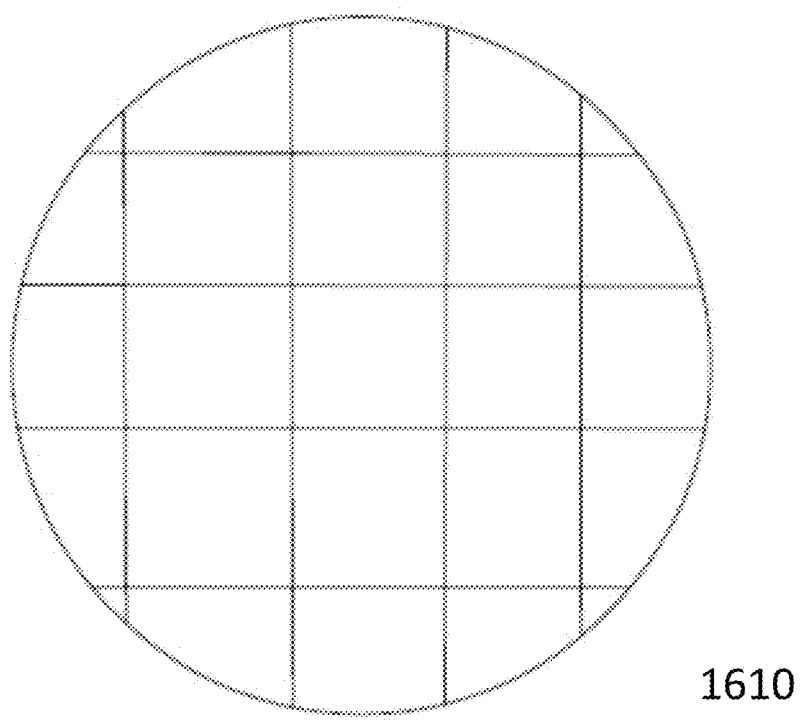
FIG. 16 shows two examples of substrates (e.g., wafers) and segments thereof—wafer 1610 with segments thereof (e.g., arranged in a grid-like pattern), and wafer 1620 with segments thereof (e.g., arranged in a concentric circle pattern)
Figure 16:
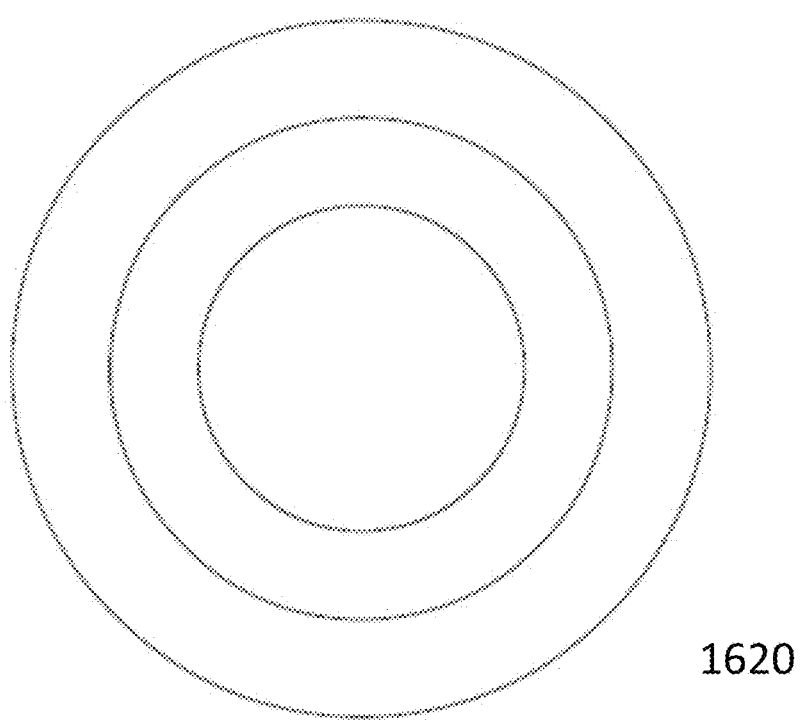

The method 1500 may comprise receiving or generating actual sequencing signals that represent at least a part of the genome of the genus. The actual sequencing signals may be generated by imaging a substrate that may include a plurality of substrate segments (as in operation 1510). FIG. 16 shows two examples of substrate (e.g., wafers) and segments thereof—wafer 1610 with segments thereof (e.g., arranged in a grid-like pattern), and wafer 1620 with segments thereof (e.g., arranged in a concentric circle pattern). It will be appreciated that the substrate may be segmented in any arrangement, pattern, or configuration into any number of segments.

The method 1500 may comprise identifying different substrate segments (as in operation 1520). In some cases, the different substrate segments may be identified prior to imaging, during imaging, or subsequent to imaging. For example, prior to imaging, the substrate may be segmented into different segments which may or may not be demarcated. In another example, subsequent to imaging, the different substrate segments may be identified from one or more images from the imaging. Any number of substrate segments may be identified.

Next, the method 1500 may comprise estimating the genome of the genus by applying a first module to signals (e.g., from among the actual sequencing signals) associated with a first substrate segment of the plurality of substrate segments and applying a second module that differs from the first module on signals (e.g., from among the actual sequencing signals) associated with a second substrate segment of the plurality of substrate segments. A different module may be applied to each of the different substrate segments. A module may be applied to multiple different substrate segments. In some cases, a set of identified substrate segments may be grouped into a plurality of groups, and a different module may be applied to each group such that the same module is applied to each member of a group. A module may comprise a model as described elsewhere herein.

In some embodiments, the plurality of substrate segments are determined based on expected or actual differences between an illumination of the plurality of substrate segments.

In some embodiments, the plurality of substrate segments are determined based on expected or actual differences between a collection or measurement of radiation from the plurality of substrate segments.

In some embodiments, the plurality of substrate segments are determined based on expected or actual distribution of chemical materials over the plurality of substrate segments.

In some embodiments, the plurality of substrate segments are determined based on expected or actual distribution of samples or sample sources over the plurality of substrate segments. For example, such samples (e.g., comprising a plurality of beads, each bead comprising a clonal population of amplified products) may be immobilized at different substrate segments.

In some embodiments, the plurality of substrate segments comprise a same shape and/or size.

In some embodiments, at least two of the plurality of substrate segments differ by at least one of shape and size.

Provided is a method for estimating a genome of a genus.

The method may comprise receiving or generating actual sequencing signals that represent at least a part of the genome of the genus; wherein the actual sequencing signals belong to at least one image of at least one part of a substrate that is linked to multiple DNA beads.

Next, the method may comprise estimating the genome of the genus by applying at least one model to the actual sequencing signals.

Computer Systems

Figure 9:
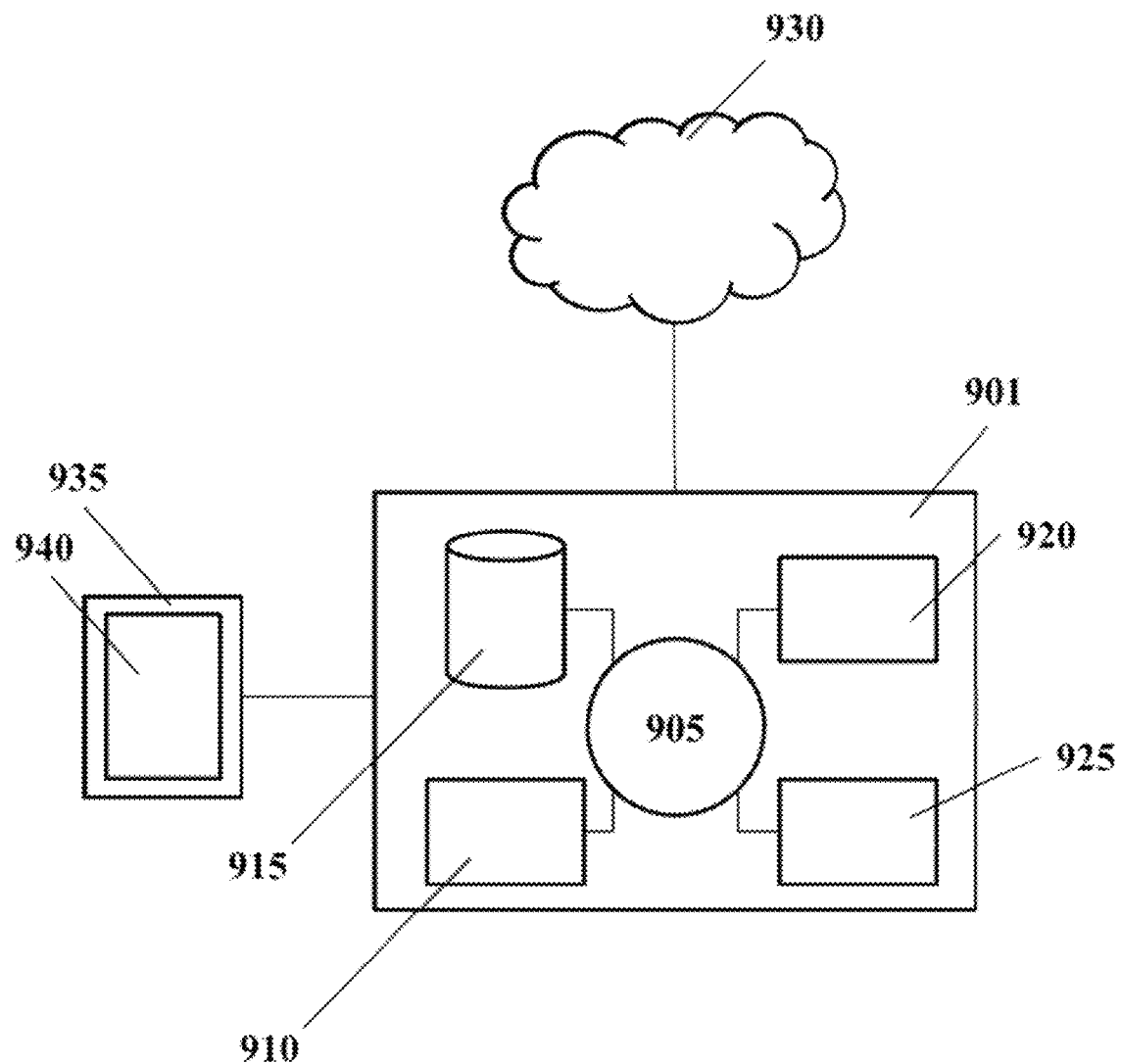
FIG. 9 shows a computer system that is programmed or otherwise configured to implement methods provided herein.

The present disclosure provides computer systems that are programmed to implement methods of the disclosure. FIG. 9 shows a computer system 901 that is programmed or otherwise configured to, for example, perform one or more operations of methods 100, 200, 300, 600, and 700.

The computer system 901 can regulate various aspects of analysis, calculation, and generation of the present disclosure, such as, for example, performing one or more operations of methods 100, 200, 300, 600, and 700. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet.

The network 930 in some cases is a telecommunication and/or data network. The network 930 can include one or more computer servers, which can enable distributed computing, such as cloud computing. For example, one or more computer servers may enable cloud computing over the network 930 ("the cloud") to perform various aspects of analysis, calculation, and generation of the present disclosure, such as, for example, performing one or more operations of methods 100, 200, 300, 600, and 700. Such cloud computing may be provided by cloud computing platforms such as, for example, Amazon Web Services (AWS), Microsoft Azure, Google Cloud Platform, and IBM cloud. The network 930, in some cases with the aid of the computer system 901, can implement a peer-to-peer network, which may enable devices coupled to the computer system 901 to behave as a client or a server.

The CPU 905 may comprise one or more computer processors and/or one or more graphics processing units (GPUs). The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine-readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, a visual display indicative of sequencing signals, actual sequencing signals, accurate sequencing signals, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, perform one or more operations of methods 100, 200, 300, 600, and 700.

EXAMPLES

Example 1

Figure 17:
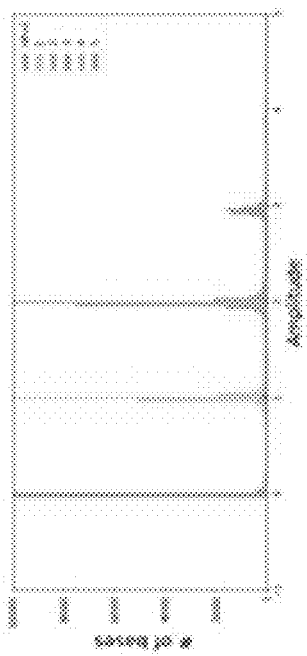
FIG. 17 shows an example of a histogram plotted of the number of bases of each of the raw sequencing signals having a given amplitude (left) and a histogram of the processed signals showing narrow distributions of a number of bases of the processed sequences having amplitudes of about 0, 1, 2, and 3 (right).
Figure 17:
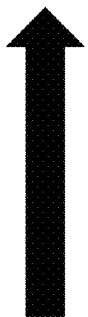
Figure 17:
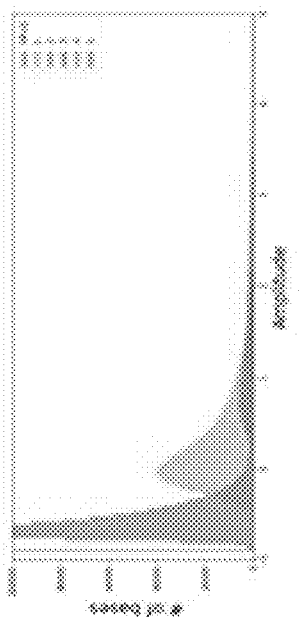

Using systems, methods, and media of the present disclosure, raw sequencing signals are generated from a plurality of nucleic acids. As shown in FIG. 17, a histogram is plotted of the number of bases of each of the raw sequencing signals having a given amplitude. A trained neural network is applied to the raw sequencing signals in order to identify and deconvolve systematics of the raw sequencing signals (such as phasing, signal decay, and context), shown in panel A, in order to generate processed sequencing signals (e.g., corrected or accurate sequencing signals), shown in panel B. A histogram of the processed signals (FIG. 17) shows narrow distributions of a number of bases of the processed sequences having amplitudes of about 0, 1, 2, and 3. The processed sequencing signals were produced without the use of a reference, thereby improving accuracy of sequence calling (e.g., sequences containing homopolymers).

Example 2

Using systems, methods, and media of the present disclosure, a neural network is trained to produce a "ground truth" mapping between a plurality of input sequencing signals of a human or other large genome (e.g., generated from a plurality of nucleic acids) and a plurality of output sequences (e.g., comprising a plurality of base calls). First, base calling is performed on the plurality of input sequencing signals, thereby producing a plurality of initial sequences. This may be performed using a full base calling model (e.g., based on a large genome such as the human genome). The plurality of initial sequences may optionally be HpN-truncated, such that all homopolymers (e.g., of length, 2, 3, 4, . . . ) in the initial sequences are truncated to a length of 1 (e.g., represented by a single base) or another small number N, in order to ensure a low error rate of alignment. Next, the HpN-truncated sequences are aligned to a matching HpN-truncated human reference (e.g., the human genome that is HpN-truncated). Next, a training set is constructed using some or all of the HpN-aligned sequences (as outputs) and the associated sequencing signals (as inputs). Next, a neural network is trained using this training set, thereby producing a trained neural network.

Alternatively or in combination, at least a portion of the HpN-truncated sequences may be aligned to a matching *E. coli* (or other smaller genome) reference. A training set may be constructed using some or all of the HpN-aligned sequences (as outputs) and the associated sequencing signals (as inputs). A neural network may be trained using this training set, thereby producing a trained neural network. Existing models may be tested against the training set in order to select a model based on accuracy (e.g., the model that minimizes the base calling error).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for generating a training set, the method comprising:
    obtaining a first trained algorithm comprising a first mapping between actual reference sequencing signals and trusted reference sequencing signals, wherein the actual reference sequencing signals and the trusted reference sequencing signals comprise analog signals generated at least in part by sequencing nucleic acids using a high-throughput sequencer, wherein the actual reference sequencing signals and the trusted reference sequencing signals represent parts of a reference genome of a first genus;
    obtaining actual sequencing signals corresponding to a second genome of a second genus that differs from the first genus, wherein the reference genome is smaller than the second genome; and
    generating the training set for training a second trained algorithm comprising a second mapping between the actual sequencing signals corresponding to the second genome and trusted sequencing signals corresponding to the second genome, wherein the training set is generated based at least in part on applying the first mapping to the actual sequencing signals corresponding to the second genome.

2. The method of claim 1, wherein the second genome is at least a portion of a human genome.

3. The method of claim 2, wherein the first trained algorithm comprises a first neural network, and wherein the second trained algorithm comprises a second neural network.

4. The method of claim 3, further comprising training the second neural network, using the training set, to map the actual sequencing signals corresponding to the second genome to the trusted sequencing signals corresponding to the second genome.

5. The method of claim 3, wherein generating the training set comprises aligning the actual sequencing signals corresponding to the second genome to the trusted reference sequencing signals.

6. The method of claim 3, further comprising training the first neural network at least in part by aligning the actual reference sequencing signals to the trusted reference sequencing signals.

7. The method of claim 6, wherein training the first neural network comprises aligning, using a first alignment process, the actual reference sequencing signals to the trusted reference sequencing signals; wherein generating the training set comprises aligning, using a second alignment process, the actual sequencing signals to the trusted reference sequencing signals; and wherein the first alignment process consumes less resources than the second alignment process.

8. The method of claim 7, wherein the first alignment process comprises determining correlations between the actual reference sequencing signals and different parts of the trusted reference sequencing signals.

9. The method of claim 7, wherein the second alignment process comprises using a hash-based search.

10. The method of claim 3, further comprising training the first neural network at least in part by performing one or more iterations of:
    selecting a portion of the actual reference sequencing signals and a portion of the trusted reference sequencing signals associated therewith;
    using the first neural network to process the selected portion of the actual reference sequencing signals to produce first neural network output signals;
    determining an error that represents a difference between the first neural network output signals and the selected portion of the trusted reference sequencing signals; and
    configuring the first neural network by backpropagating the error.

11. The method of claim 10, wherein the first neural network comprises a regression network.

12. The method of claim 11, wherein the regression network comprises a fully connected regression network.

13. The method of claim 11, wherein the regression network comprises an input layer that comprises one neuron per value of the actual reference sequencing signals, and a plurality of intermediate layers that are larger than the input layer.

14. The method of claim 3, wherein generating the training set comprises truncating the actual sequencing signals and the trusted reference sequencing signals, and aligning the truncated actual sequencing signals to the truncated trusted reference sequencing signals.

15. The method of claim 3, further comprising using the second neural network to process the actual sequencing signals and additional information of a type that differs from the actual sequencing signals.

16. The method of claim 15, wherein the additional information comprises information regarding background noise of the actual sequencing signals.

17. The method of claim 15, wherein the additional information comprises sequencing signals obtained from a preamble of the sequencing.

18. The method of claim 15, wherein the additional information comprises local information corresponding to a vicinity of the actual sequencing signals.

19. The method of claim 15, wherein the additional information comprises flow information indicative of at least one of a flow base and a flow position of the actual sequencing signals.

20. A method for estimating, based at least in part on a reference genome of a first genus, a second genome of a second genus, the method comprising:
    for each of a plurality of parts of the second genome:
        obtaining actual sequencing signals that represent the part of the second genome; and
        estimating the part of the second genome based at least in part on the actual sequencing signals;
    wherein the estimating comprises applying a machine learning classifier to the actual sequencing signals;
    wherein the machine learning classifier is trained to provide a second mapping between the actual sequencing signals and trusted sequencing signals corresponding to the second genome, wherein the actual sequencing signals and the trusted sequencing signals comprise analog signals generated at least in part by sequencing nucleic acids using a high-throughput sequencer;
    wherein the second mapping is generated based at least in part on a first mapping between actual reference sequencing signals and trusted reference sequencing signals corresponding to the reference genome; and
    wherein the actual reference sequencing signals and the trusted reference sequencing signals represent parts of the reference genome of the first genus that differs from the second genus, wherein the reference genome is smaller than the second genome.

* * * * *